United States Patent
Sauve et al.

(10) Patent No.: US 9,290,791 B2
(45) Date of Patent: Mar. 22, 2016

(54) REAGENTS AND METHODS FOR SIRTUIN CAPTURE

(75) Inventors: Anthony A. Sauve, New Rochelle, NY (US); Yana Cen, New York, NY (US)

(73) Assignee: CORNELL UNIVERSITY, Ithaca, NY (US)

( * ) Notice: Subject to any disclaimer, the term of this patent is extended or adjusted under 35 U.S.C. 154(b) by 322 days.

(21) Appl. No.: 13/698,561

(22) PCT Filed: May 18, 2011

(86) PCT No.: PCT/US2011/037023
§ 371 (c)(1),
(2), (4) Date: Nov. 16, 2012

(87) PCT Pub. No.: WO2011/146636
PCT Pub. Date: Nov. 24, 2011

(65) Prior Publication Data
US 2013/0065248 A1    Mar. 14, 2013

Related U.S. Application Data

(60) Provisional application No. 61/345,970, filed on May 18, 2010.

(51) Int. Cl.
| | |
|---|---|
| G01N 33/573 | (2006.01) |
| C12N 9/98 | (2006.01) |
| A61K 38/06 | (2006.01) |
| C07K 5/00 | (2006.01) |
| C07K 7/00 | (2006.01) |
| C07K 16/00 | (2006.01) |
| C07K 17/00 | (2006.01) |
| C07H 19/00 | (2006.01) |
| C12Q 1/34 | (2006.01) |

(52) U.S. Cl.
CPC .............. *C12Q 1/34* (2013.01); *C12Q 2334/00* (2013.01); *G01N 2333/918* (2013.01); *G01N 2500/00* (2013.01)

(58) Field of Classification Search
CPC .. C12Q 1/34; C12Q 2334/00; G01N 2500/00; G01N 2333/918
See application file for complete search history.

(56) References Cited

U.S. PATENT DOCUMENTS 7,351,542 B2    4/2008   Verdin et al.

FOREIGN PATENT DOCUMENTS

WO    WO 2009/026701 A1    3/2009

OTHER PUBLICATIONS

Ahn et al., γ-Tocotrienol Inhibits Nuclear Factor-B Signaling Pathway through Inhibition of Receptor-interacting Protein and TAK1 Leading to Suppression of Antiapoptotic Gene Products and Potentiation of Apoptosis, *J. Biol. Chem.*, 282:809-820 (2007).

Ahuja et al., Regulation of Insulin Secretion by SIRT4, a Mitochondrial ADP-ribosyltransferase, *J. Biol. Chem.*, 282(46): 33583-33589 (2007).

Allart et al., A Stable Bis-Allyloxycarbonyl Biotin Aldehyde Derivative for Biotinylation via Reductive Alkylation: Application to the Synthesis of a Biotinylated Doxorubicin Derivative, *Bioconjugate Chem.* 14:187-194 (2003).

Cen, Y., Sirtuins inhibitors: the approach to affinity and selectivity, *Biochem Biophys Acta.*, 1804(8): 1635-44 (Epub Nov. 18, 2009).

Choudhary et al., Lysine Acetylation Targets Protein Complexes and Co-Regulates Major Cellular Functions, *Science*, 325:834-840 (2009).

Dali-Youcef et al., Sirtuins: The 'magnificent seven', function, metabolism and longevity, *Annals of Medicine*, 39:335-345 (2007).

Fatkins et al., N-epsilon-Thioacetyl-lysine: A multi-facet functional probe for enzymatic protein lysine Nε-deacetylation, *Bioorg. Med. Chem. Lett.*, 16:3651-3656 (2006).

(Continued)

*Primary Examiner* — Lawrence E Crane
(74) *Attorney, Agent, or Firm* — Leydig, Voit & Mayer, Ltd.

(57) ABSTRACT

The invention provides a method of preparing a sirtuin complex, a method for detecting a sirtuin in a sample, and a method of screening for compounds which inhibit the deacetylase activity of a sirtuin. The method includes (a) providing a sirtuin substrate having the formula:

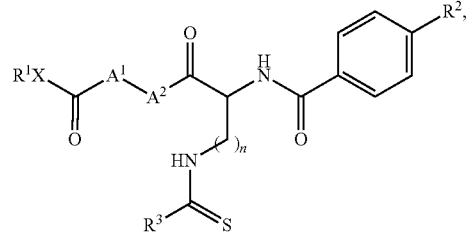

(b) providing NAD⁺ or an NAD⁺ analog having the formula:

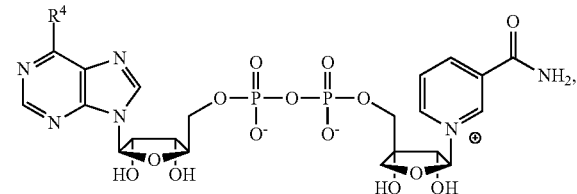

and (c) providing a sirtuin, wherein $R^1$-$R^4$, $A^1$, $A^2$, and n are as defined herein.

13 Claims, 13 Drawing Sheets

(56) References Cited

OTHER PUBLICATIONS

Ford et al., Mammalian Sir2 homolog SIRT7 is an activator of RNA polymerase I transcription, *Genes Dev.*, 20:1075-1080 (2006).

Gan et al., Paths of Convergence: Sirtuins in Aging and Neurodegeneration, *Neuron*, 58: 10-14 (2008).

Huhtiniemi, et al., N(epsilon)-Modified lysine containing inhibitors for SIRT1 and SIRT2, *Bioorganic and Medicinal Chemistry Epub*, 18(15): 5616-25 (2010).

Imai et al., Ten years of NAD-dependent SIR2 family deacetylases: implications for metabolic diseases, *Trends In Pharmacological Sciences*, 31(5): 212-220 (2010).

Jing et al., SIRT2 Regulates Adipocyte Differentiation through FoxO1 Acetylation/Deacetylation, *Cell Metabolism*, 6:105-114 (2007).

Kiviranta et al., N(epsilon)-Thioacetyl-Lysine-Containing Tri-, Tetra-, and Pentapeptides as SIRT1 and SIRT2 Inhibitors, *J. Med. Chem.*, 52(7): 2153-2156 (2009).

Liszt et al., Mouse Sir2 Homolog SIRT6 Is a Nuclear ADP-ribosyltransferase, *J. Biol. Chem.*, 280(22): 21313-21320 (2005).

Michishita et al., Evolutionarily Conserved and Nonconserved Cellular Localizations and Functions of Human SIRT Proteins, *Mol. Biol. Cell*, 16: 4623-4635 (2005).

Nakagawa et al., SIRT5 Deacetylates Carbamoyl Phosphate Synthetase 1 and Regulates the Urea Cycle, *Cell*, 137: 560-570 (2009).

Nemoto et al., SIRT1 Functionally Interacts with the Metabolic Regulator and Transcriptional Coactivator PGC-1α, *J. Biol. Chem.*, 280(16): 16456-16460 (2005).

North et al., The Human Sir2 Ortholog, SIRT2, Is an NAD+-Dependent Tubulin Deacetylase, *Molecular Cell*, 11: 437-444 (2003).

Picard et al., Sirt1 promotes fat mobilization in white adipocytes by repressing PPAR-gamma, *Nature*, 429: 771-776 (2004).

Sadamoto et al., Control of Bacteria Adhesion by Cell-Wall Engineering, *J. Am. Chem. Soc.*, 126: 3755-3761 (2004).

Sauve et al., SIR2: The Biochemical Mechanism of NAD+-Dependent Protein Deacetylation and ADP-Ribosyl Enzyme Intermediates, *Current Medicinal Chemistry*, 11: 807-826 (2004).

Schwer et al., Reversible lysine acetylation controls the activity of the mitochondrial enzyme acetyl-CoA synthetase 2, *Proc. Nat. Acad. Sci.*, 103(27): 10224-10229 (2006).

Suzuki, et al., Identification of a cell-active non-peptide sirtuin inhibitor containing N-thioacetyl lysine, *Bioorg Med Chem Lett.*, 19(19): 5670-5672 (2009).

Vakhrusheva et al., Sirt7 Increases Stress Resistance of Cardiomyocytes and Prevents Apoptosis and Inflammatory Cardiomyopathy in Mice, *Circulation Research*, 102: 703-710 (2008).

Vakhrusheva et al., Sirt7-Dependent Inhibition Of Cell Growth And Proliferation Might Be Instrumental To Mediate Tissue Integrity During Aging, *J. Physiol. Pharm.*, 59: 201-212 (2008).

Wang et al., SIRT2 deacetylates FOXO3a in response to oxidative stress and caloric restriction, *Aging Cell*, 6: 505-514 (2007).

Zhao et al., Regulation of Cellular Metabolism by Protein Lysine Acetylation, *Science*, 327: 1000-1004 (2010).

Azido-Biotin

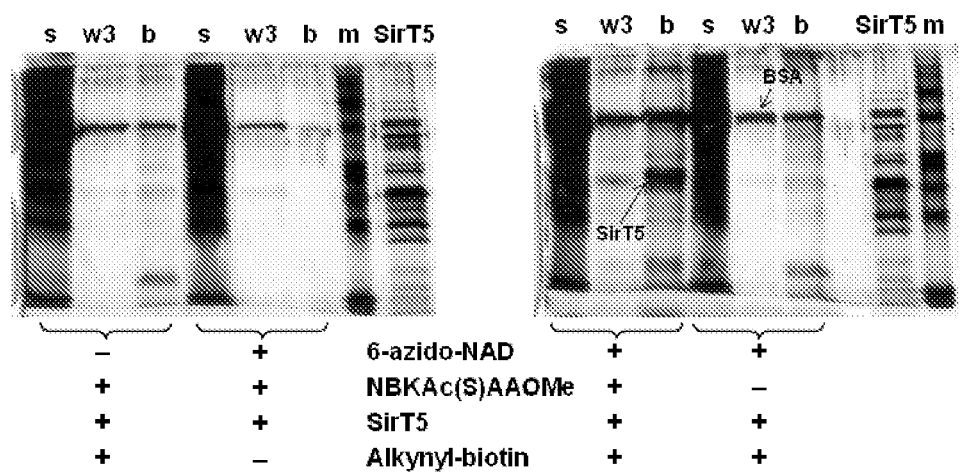
FIG. 6 (con't)

FIG. 7 (con't)
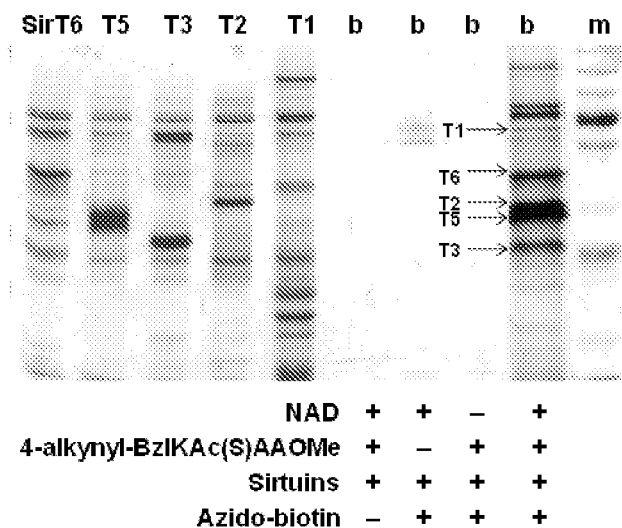
FIG. 8
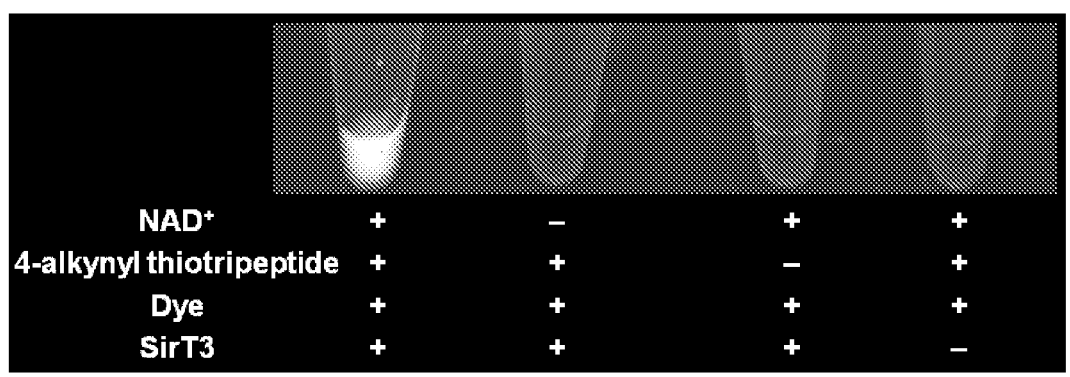

REAGENTS AND METHODS FOR SIRTUIN CAPTURE

CROSS-REFERENCE TO A RELATED APPLICATION

This patent application is the U.S. national phase of International Patent Application No. PCT/US2011/037023, filed May 18, 2011, which claims the benefit of U.S. Provisional Patent Application No. 61/345,970, filed May 18, 2010, which is incorporated by reference.

STATEMENT REGARDING FEDERALLY SPONSORED RESEARCH AND DEVELOPMENT

This invention was made with United States Government support under Grant Number R01 DK 074366 awarded by the the National Institutes of Health. The United States Government has certain rights in this invention.

BACKGROUND OF THE INVENTION

The sirtuin enzymes are $NAD^+$ dependent acetyl-lysine deacetylases. Their catalytic mechanism utilizes $NAD^+$ as a substrate to effect removal of an acetyl group from an acetyl-lysine residue of the protein substrate to form nicotinamide, 2' O-acetyl-ADP-ribose (AADPR), and the deacetylated substrate (Sauve et al., *Curr. Med. Chem.*, 11: 807-826 (2004)). In mammals, the seven family members of the sirtuin enzymes (SirT1 to SirT7) are responsible for the regulation of a broad range of cellular processes through their vast array of substrates and sub-cellular locations (Michishita et al., *Mol. Biol. Cell*, 16: 4623-4653 (2005)). SirT1 is localized to the nucleus and is responsible for modulating cellular stress response through the deacetylation of histones and transcription factors (Dali-Youcef et al., *Ann. Med.*, 39: 335 (2007); Motta et al., *Cell*, 137: 560-570 (2009); Nemoto et al., *J. Biol. Chem.*, 280: 16456 (2005); Picard et al., *Nature*, 429: 771-776 (2004)). SirT2, localized predominately in the cytosol, has been identified as an α-tubulin deacetylase (North et al., *Mol. Cell*, 11: 437-444 (2003)), however, the protein has been shown to translocate to the nucleus to regulate the deacetylation of FOXO transcription factors (North et al., supra; Wang et al., *Aging Cell*, 6: 505-514 (2007); Jing et al., *Cell Metab.*, 6: 105-114 (2007)). SirT3 and SirT5 are mitochondrial deacetylases, the former being shown to deacetylate enzymes involved in energy regulation and metabolism (Schwer et al., *Proc. Nat. Acad. Sci. U.S.A.*, 103: 10224-10229 (2006); Ahn et al., *J. Biol. Chem.*, 282: 33583-33589 (2007)). SirT5 activity is involved in regulation of the urea cycle, although much is still unknown regarding the enzyme's physiological substrates (Nakagawa et al., *Cell*, 137: 560-570 (2009)). SirT6, localized to the nucleus, is crucial for telomere maintenance through the deacetylation of histone H3, and it also modulates Hif1alpha and NFκB activities.

Protein acetylation has been identified in the nucleus, cytoplasm, and mitochondria. Furthermore, several independent proteomic studies have identified the number of acetylated proteins to be in the thousands, thereby highlighting the potential global role of sirtuin deacetylation in cell maintenance and function (Choudhary et al., *Science*, 325: 834-840 (2009); Yang et al., *Cell*, 31: 449-461 (2008); Zhao et al., *Science*, 327: 1000-1004 (2010)). The most characterized activity catalyzed by sirtuins is the deacetylation of cellular proteins, shown to be a function of SirT1, SirT2, SirT3, SirT5, and SirT6. SirT6 has also been shown to catalyze auto-ADP-ribosyl transfer; however, the enzymatic consequence and physiological relevance of this modification remains unknown (Liszt et al., *J. Biol. Chem.*, 280: 21313-21320 (2005)). By far, the mitochondrial SirT4 and the nucleolar SirT7 are the least characterized of the sirtuin family members. SirT4 has been reported to catalyze ADP-ribosyl transfer to glutamate dehydrogenase and has been implicated in the regulation of insulin secretion; although, the mechanism of catalysis is undetermined (Ahn et al., supra.). SirT7 has been implicated in the regulation of cell proliferation, prevention of cardiomyocyte death, and ribosomal DNA transcription (Vakhrusheva et al., *Circ. Res.*, 102: 703-710 (2008); Vakhrusheva et al., *J. Physiol. Pharm.*, 59: 201-212 (2008); Ford et al., *Genes Dev.*, 20: 1075-1080 (2006)). These findings were observed as consequences of SirT7 knockdown or mutation, and both the enzymatic activity and potential substrates are uncharacterized.

Current methodologies have implicated the involvement of sirtuins in processes that protect against a number of age-related processes and diseases including Type-II diabetes (Imai et al., *Trends Pharmacol Sci.*, 31: 212-220 (2010)) and Alzheimer's disease (Gan et al., *Neuron*, 58: 10-14 (2008)). However, many of the studies, such as transgenic models of overexpression or enzyme knock-down, are limited to qualitative observations that provide information regarding the global cellular effects of sirtuin activity. There is a demand for the development of a tool that possesses the ability to specifically probe for sirtuin activity in a biologically and pathologically relevant context, rather than using downstream cellular effects as an activity readout.

BRIEF SUMMARY OF THE INVENTION

The invention provides a method of preparing a sirtuin complex, which method comprises (i) providing a first component comprising a sirtuin substrate comprising a thioamide moiety, (ii) providing a second component comprising $NAD^+$ or an $NAD^+$ analog, (iii) providing a third component comprising a sirtuin, and (iv) combining the first, second, and third components such that a sirtuin complex is formed, wherein the sirtuin complex comprises the sirtuin, the sirtuin substrate, and $NAD^+$ or an $NAD^+$ analog.

The invention also provides a method for detecting a sirtuin in a sample, which method comprises (i) providing a first component comprising a sirtuin substrate comprising a thioamide moiety, (ii) providing a second component comprising $NAD^+$ or an $NAD^+$ analog, (iii) providing a sample suspected of comprising a sirtuin, (iv) combining the first and second components and sample such that a first mixture is formed, in which the sirtuin, if present in the sample, forms a sirtuin complex, (v) contacting the first mixture containing the sirtuin complex with a label compound to form a second mixture comprising a labeled sirtuin complex, wherein the label compound is covalently bonded to the sirtuin complex, (vi) separating the labeled sirtuin complex from other components of the second mixture to form a third mixture, and (vii) detecting whether the labeled sirtuin complex is present in the third mixture, wherein the detection of the labeled sirtuin complex in the third mixture indicates the presence of the sirtuin in the sample.

The invention further provides a method of screening for compounds which inhibit the deacetylase activity of a sirtuin, which method comprises (i) providing a first test mixture comprising (a) a sirtuin substrate comprising a thioamide moiety and a first reactive moiety, (b) $NAD^+$, and (c) a candidate compound, (ii) adding a sirtuin to the first test mixture to form a second test mixture, (iii) incubating the second test mixture for a period of time, (iv) adding a label compound comprising a second reactive moiety to the second test mixture to form a third test mixture, wherein the first and second reactive moieties react to form at least one covalent bond between the sirtuin substrate and the label compound, (v) contacting the third test mixture with a solid phase so as to immobilize components comprising the label compound and to form a test solid phase, (vi) separating uncomplexed components from the test solid phase, (vii) subjecting the test solid phase to conditions to regenerate the sirtuin, if present, from the test solid phase and to form a fourth test mixture, and (viii) determining if the sirtuin is present in a decreased amount in the fourth test mixture relative to the amount of sirtuin added to the first test mixture, wherein a decreased amount of the sirtuin in the fourth test mixture relative to the amount of sirtuin that would be observed in the absence of the candidate compound indicates that the candidate compound is an inhibitor of the sirtuin.

The invention also provides a compound of the formula:

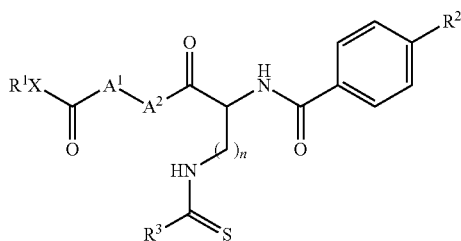

wherein $R^1$ is hydrogen, optionally substituted alkyl or optionally substituted aryl, X is O or $NR^7$, $R^2$ is selected from the group consisting of azido, nitro, alkylazido, arylazido, alkyarylazido, arylalkylazido, alkyloxyamino, aryloxyamino, alkyaryloxyamino, arylalkyloxyamino, alkynyl, cycloalkynyl, and alkynylarylalkylcarbonyl, $A^1$ and $A^2$ are the same or different and are amino acids, $R^3$ is alkyl, $R^7$ is hydrogen or alkyl, and n is an integer of 1 to 10.

The invention further provides a compound of the formula:

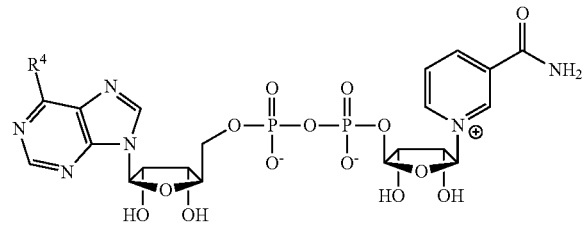

wherein $R^4$ is alkyloxyamino, aminooxyethyleneoxyamino, azidooxyethyleneoxyamino, aminooxy(polyethyleneoxy)amino, or azido(polyethyleneoxy)amino.

BRIEF DESCRIPTION OF THE SEVERAL VIEWS OF THE DRAWING(S)

FIG. 8 illustrates tubes containing eluents from various samples after quick spin DNA columns.

DETAILED DESCRIPTION OF THE INVENTION

In an embodiment, the invention provides a method of preparing a sirtuin complex, which method comprises (i) providing a first component comprising a sirtuin substrate comprising a thioamide moiety, (ii) providing a second component comprising $NAD^+$ or an $NAD^+$ analog, (iii) providing a third component comprising a sirtuin, and (iv) combining the first, second, and third components such that a sirtuin complex is formed, wherein the sirtuin complex comprises the sirtuin, the sirtuin substrate, and $NAD^+$ or an $NAD^+$ analog.

Figure 1:
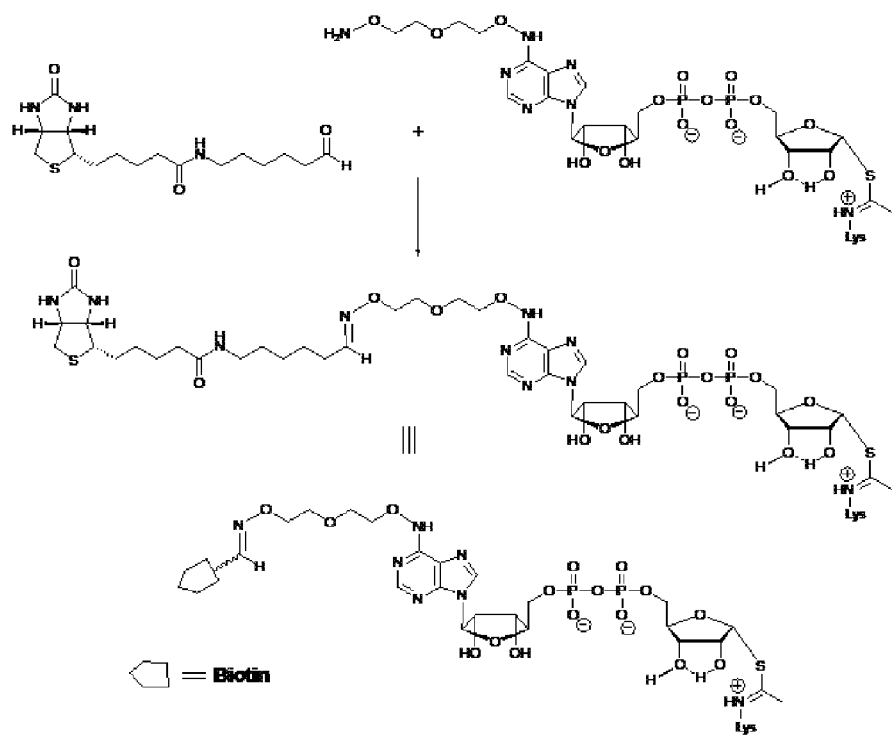
FIG. 1 illustrates the formation of a representative biotinylated sirtuin complex.

$N^\epsilon$-thioacetyl-lysine peptide analogs of sirtuin substrates are known to inhibit SirT-1, 2-, and 3-catalyzed deacetylation with observed affinities in the nanomolar to low micromolar range. Thioacetylated peptide inhibitors are mechanism-based and are suggested to act via the formation of an unreactive 1'-S-imidate intermediate formed between the thioacetyl-lysine moiety and the anomeric carbon of the $NAD^+$ co-substrate as illustrated in FIG. 1. The intermediate formed is high-affinity and temporally persistent, and is kinetically stable to the forward deacetylation activity of the enzyme. Incorporation of a reactive moiety on either the thiopeptide sirtuin inhibitor or the NAD+ molecule allows for the capture or detection of the stable intermediate. A thioacetylated peptide inhibitor is interchangeably referred to herein as a sirtuin substrate comprising a thioamide moiety. The sirtuin, the sirtuin substrate comprising a thioamide moiety, and $NAD^+$ or an $NAD^+$ analog combine to form a sirtuin complex.

In an embodiment, the sirtuin substrate is a substrate for at least one sirtuin selected from the group consisting of SirT1, SirT2, SirT3, SirT4, SirT5, SirT6, and SirT7, wherein SirT1, SirT2, SirT3, SirT4, SirT5, SirT6, and SirT7 are $NAD^+$-dependent protein deacetylases. In a preferred embodiment, the sirtuin substrate is a substrate for each of SirT1, SirT2, SirT3, SirT4, SirT5, SirT6, and SirT7.

In an embodiment, the sirtuin substrate comprises a tripeptide. In certain embodiments, the tripeptide comprises an amino acid of the formula: $H_2N$—$CH[(CH_2)_n$—$NHC(=S)CH_3]$—COOH wherein n is an integer of 1 to 10.

In certain embodiments, the sirtuin substrate comprises an oxyamino group, an azido group, a nitro group, or an alkynyl group.

In a preferred embodiment, the sirtuin substrate has the formula:

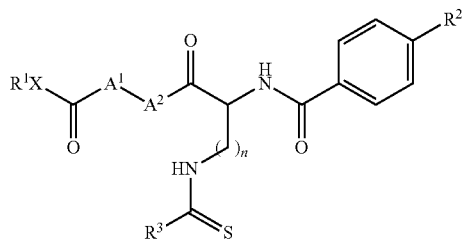

wherein $R^1$ is hydrogen, optionally substituted alkyl or optionally substituted aryl, X is O or $NR^7$, $R^2$ is selected from the group consisting of azido, nitro, alkylazido, arylazido, alkyarylazido, arylalkylazido, alkyloxyamino, aryloxyamino, alkyaryloxyamino, arylalkyloxyamino, alkynyl, cycloalkynyl, and alkynylarylalkylcarbonyl, $A^1$ and $A^2$ are the same or different and are amino acids, $R^3$ is alkyl, $R^7$ is hydrogen or alkyl, and n is an integer of 1 to 10.

In certain embodiments, X is O.

In certain embodiments, $R^2$ is selected from the group consisting of azido, nitro, —$CH_2ONH_2$,

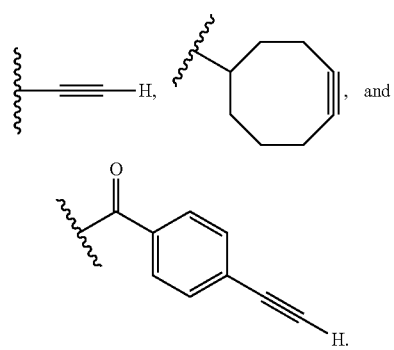

In certain preferred embodiments, the sirtuin substrate is selected from the group consisting of

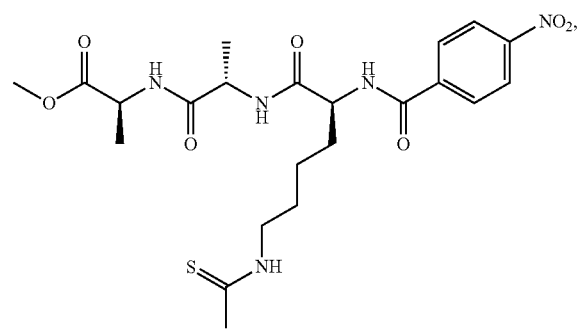

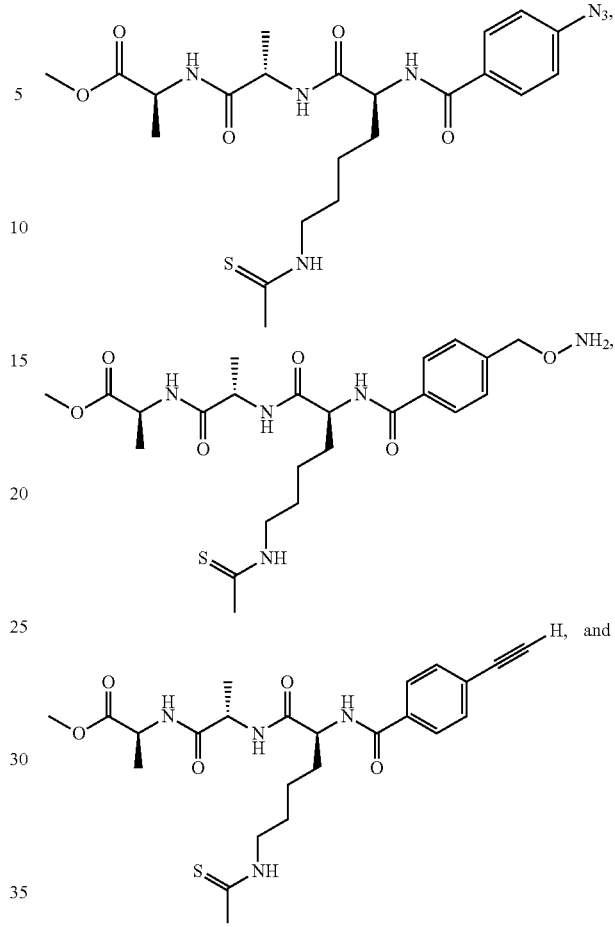

In certain embodiments, the sirtuin substrate has the formula:

wherein m is an integer of 1 to 10, wherein $R^4$ and $R^5$ are independently selected from the group consisting of alkyl, aryl, alkoxyalkyl, alkenyl, arylalkyl, and heterocyclyl, or, taken together, form a 3- to 6-membered nitrogen-containing ring, and wherein $R^8$ is alkyl, and wherein $R^7$ is selected from the group consisting of hydrogen, alkyl, halo, azido, nitro, alkylazido, arylazido, alkyarylazido, arylalkylazido, alkyloxyamino, aryloxyamino, alkyaryloxyamino, arylalkyloxyamino, alkynyl, cycloalkynyl, and alkynylarylalkylcarbonyl.

In certain embodiments, m is 4. In certain preferred embodiments, $R^4$ and $R^5$ are both methyl or both 2-methoxyethyl, $R^4$ is ethyl and $R^5$ is phenyl, $R^4$ is methyl and $R^5$ is allyl, $R^4$ is trimethylsilylmethyl and $R^5$ is benzyl, $R^4$ is phenyl and $R^5$ is benzyl, $R^4$ is phenyl-1-ethyl and $R^5$ is benzyl, or $R^4$ and R[5] taken together form a morpholine ring, a 2-methylaziridine ring, a pyrrolidine ring, or a indoline ring.

In an embodiment, the second component is NAD[+]. In certain embodiments, the second component is an NAD[+] analog. In a preferred embodiment, the NAD[+] analog is a compound having the formula:

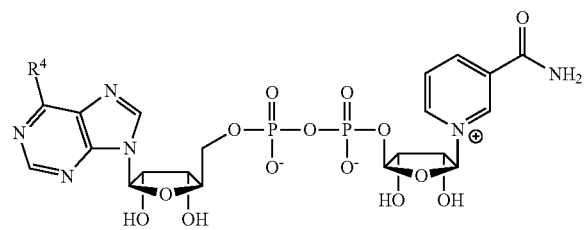

wherein R[4] is alkyloxyamino, aminooxyethyleneoxyamino, azidooxyethyleneoxyamino, aminooxy(polyethyleneoxy)amino, or azido(polyethyleneoxy)amino.

In more preferred embodiments, the NAD[+] analog is

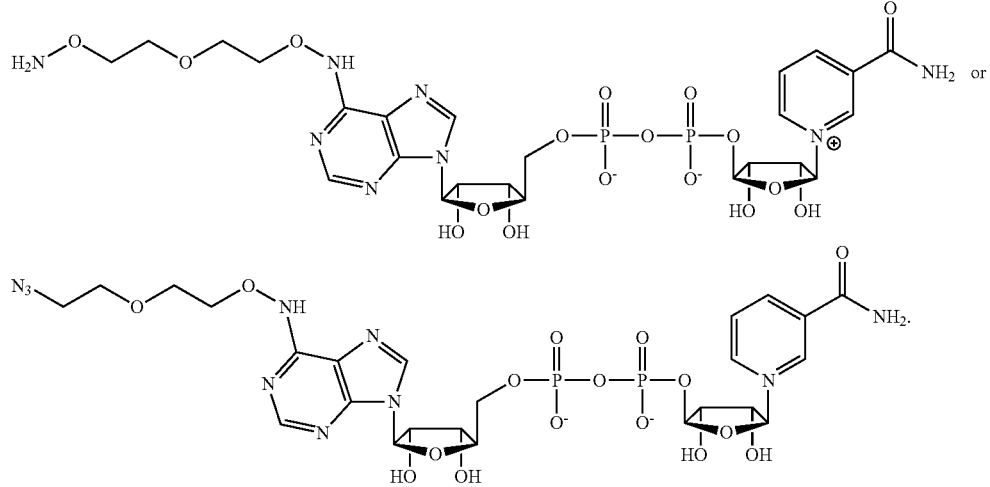

In an embodiment, the invention provides a sirtuin complex prepared by a method comprising (i) providing a first component comprising a sirtuin substrate comprising a thioamide moiety, (ii) providing a second component comprising NAD[+] or an NAD[+] analog, (iii) providing a third component comprising a sirtuin, and (iv) combining the first, second, and third components such that a sirtuin complex is formed, wherein the sirtuin complex comprises the sirtuin, the sirtuin substrate, and NAD[+] or an NAD[+] analog.

In an embodiment, the invention provides a method for detecting a sirtuin in a sample, which method comprises (i) providing a first component comprising a sirtuin substrate comprising a thioamide moiety, (ii) providing a second component comprising NAD[+] or an NAD[+] analog, (iii) providing a sample suspected of comprising a sirtuin, (iv) combining the first and second components and sample such that a first mixture is formed, in which the sirtuin, if present in the sample, forms a sirtuin complex, (v) contacting the first mixture containing the sirtuin complex with a label compound to form a second mixture comprising a labeled sirtuin complex, wherein the label compound is covalently bonded to the sirtuin complex, (vi) separating the labeled sirtuin complex from other components of the second mixture to form a third mixture, and (vii) detecting whether the labeled sirtuin complex is present in the third mixture, wherein the detection of the labeled sirtuin complex in the third mixture indicates the presence of the sirtuin in the sample.

The sirtuin substrate can be as recited herein in connection with the sirtuin complex. In a preferred embodiment, the sirtuin substrate is a substrate for at least one sirtuin selected from the group consisting of SirT1, SirT2, SirT3, SirT4, SirT5, SirT6, and SirT7. In a more preferred embodiment, the sirtuin substrate is a substrate for two or more, or three or more, or four or more, or five or more, or six or more, or for sirtuins SirT1, SirT2, SirT3, SirT5, and SirT6, or for the sirtuins SirT1, SirT2, SirT3, SirT4, SirT5, SirT6, and SirT7. Preferably, the sirtuin is an active sirtuin. Thus, the inventive method desirably allows for the detection of catalytically active sirtuins in biological samples as opposed to inactive or inactivated sirtuins present therein, which may not be involved in metabolic pathways in these particular biological samples.

In a preferred embodiment, the sirtuin substrate has the formula:

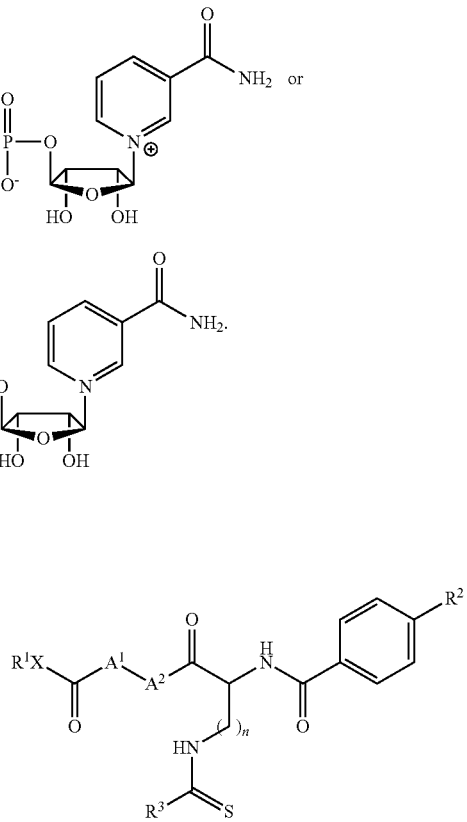

wherein R[1] is hydrogen, optionally substituted alkyl or optionally substituted aryl, X is O or NR[7], R[2] is selected from the group consisting of azido, nitro, alkylazido, arylazido, alkyarylazido, arylalkylazido, alkyloxyamino, aryloxyamino, alkyaryloxyamino, and arylalkyloxyamino, A[1] and A[2] are the same or different and are amino acids, R[3] is alkyl, R[7] is hydrogen or alkyl, and n is an integer of 1 to 10.

In another preferred embodiment, the sirtuin substrate has the formula:

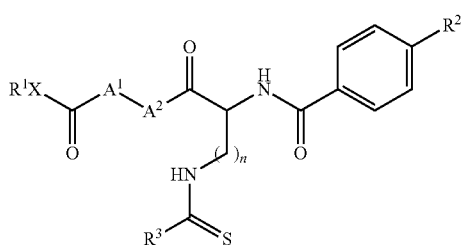

wherein R¹ is hydrogen, optionally substituted alkyl or optionally substituted aryl, X is O or NR⁷, R² is selected from the group consisting of alkynyl, cycloalkynyl, and alkynylarylalkylcarbonyl, A¹ and A² are the same or different and are amino acids, R³ is alkyl, R⁷ is hydrogen or alkyl, and n is an integer of 1 to 10.

In any of the above embodiments, the second component can be NAD⁺.

In any of the above embodiments, the second component can comprise a NAD⁺ analog having the formula:

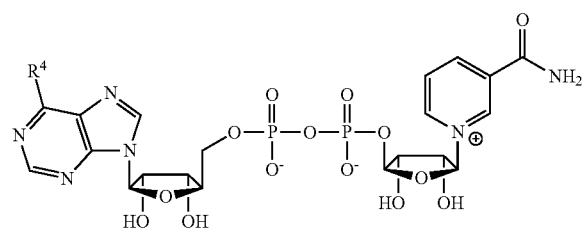

wherein R⁴ is alkyloxyamino, aminooxyethyleneoxyamino, azidooxyethyleneoxyamino, aminooxy(polyethyleneoxy)amino, or azido(polyethyleneoxy)amino.

In certain preferred embodiments, the NAD⁺ analog is

In some embodiments, the label compound is a compound of the formula: DYE-C≡C—R, wherein DYE is a dye molecule and wherein R is hydrogen or alkyl.

In some embodiments, the label compound is a compound of the formula: DYE-N₃, wherein DYE is a dye molecule.

In some embodiments, the label compound comprises a biotin moiety and an aldehyde moiety, a biotin moiety and an alkynyl moiety, or a biotin moiety and an azido moiety. A sirtuin complex comprising an oxyamino moiety can react with a label compound comprising a biotin moiety and an aldehyde moiety to form an imine bond between the oxyamino group and the aldehyde group and thus to covalently bond the label compound to the sirtuin complex. A sirtuin complex comprising an alkynyl moiety can react with a label compound comprising biotin moiety and an azido moiety to form a triazole group by cyclization of the azido moiety and the alkynyl moiety and thus to covalently bond the label compound to the sirtuin complex. A sirtuin complex comprising an azido moiety can react with a label compound comprising biotin moiety and an alkynyl moiety to form a triazole group by cyclization of the azido moiety and the alkynyl moiety and thus to covalently bond the label compound to the sirtuin complex.

In certain embodiments, the separating step (vi) comprises the following steps of (vi-1) contacting the second mixture with a solid phase so as to immobilize the labeled sirtuin complex, and (vi-2) separating uncomplexed components from the solid phase to form a third mixture comprising the solid phase and the immobilized sirtuin complex. In preferred embodiments, the separating step (vi) further comprises subjecting the solid phase to conditions to regenerate the sirtuin from the labeled sirtuin complex to form a fourth mixture. In these preferred embodiments, the method further comprises a step (vii) of detecting whether the sirtuin is in the fourth mixture, wherein the detection of the sirtuin in the fourth mixture indicates the presence of the labeled sirtuin complex in the third mixture and thus the presence of the sirtuin in the sample.

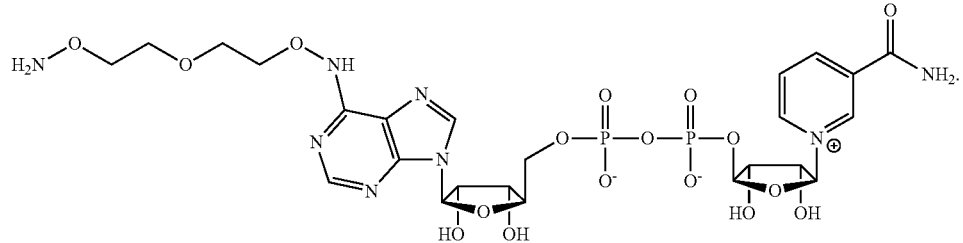

In certain preferred embodiments, the the second component comprises a NAD⁺ analog having the formula:

A label compound comprising a biotin moiety can immobilized to a solid phase comprising avidin, for example to

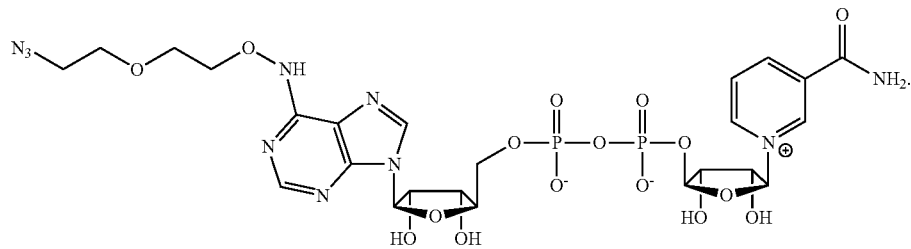

avidin agarose beads, via interaction of the biotin moiety with avidin. Thus, the sirtuin complex may be immobilized to a solid phase via the biotinylated label compound, and uncomplexed components present in the mixture can be removed by, for example, washing the beads.

The solid phase having the labeled sirtuin complex immobilized thereon is then subjected to conditions to regenerate the sirtuin from the labeled sirtuin complex. For example, the solid phase can be treated with a buffer solution to liberate the sirtuin from the labeled sirtuin complex. In some embodiments, the solid phase can be heated in SDS-loading buffer, and subsequently loaded directly onto SDS-PAGE gels, and the sirtuin liberated during gel electrophoresis.

In an embodiment, the invention provides a method of screening for compounds which inhibit the deacetylase activity of a sirtuin, which method comprises (i) providing a first test mixture comprising (a) a sirtuin substrate comprising a thioamide moiety and a first reactive moiety, (b) NAD+, and (c) a candidate compound, (ii) adding a sirtuin to the first test mixture to form a second test mixture, (iii) incubating the second test mixture for a period of time, (iv) adding a label compound comprising a second reactive moiety to the second test mixture to form a third test mixture, wherein the first and second reactive moieties react to form at least one covalent bond between the sirtuin substrate and the label compound, (v) contacting the third test mixture with a solid phase so as to immobilize components comprising the label compound and to form a test solid phase, (vi) separating uncomplexed components from the test solid phase, (vii) subjecting the test solid phase to conditions to regenerate the sirtuin, if present, from the test solid phase and to form a fourth test mixture, and (viii) determining if the sirtuin is present in a decreased amount in the fourth test mixture relative to the amount of sirtuin added to the first test mixture, wherein a decreased amount of the sirtuin in the fourth test mixture relative to the amount of sirtuin that would be observed in the absence of the candidate compound indicates that the candidate compound is an inhibitor of the sirtuin.

In certain embodiments, the sirtuin substrate has the formula:

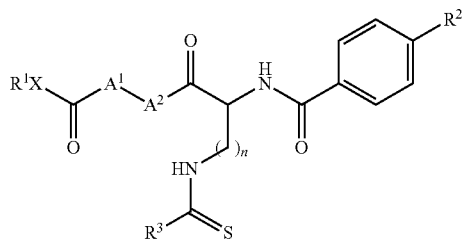

wherein $R^1$ is hydrogen, optionally substituted alkyl or optionally substituted aryl, X is O or $NR^7$, $R^2$ is selected from the group consisting of azido, nitro, alkylazido, arylazido, alkyarylazido, arylalkylazido, alkyloxyamino, aryloxyamino, alkyaryloxyamino, and arylalkyloxyamino, $A^1$ and $A^2$ are the same or different and are amino acids, $R^3$ is alkyl, $R^7$ is hydrogen or alkyl, and n is an integer of 1 to 10.

In a preferred embodiment, $R^1$ and $R^3$ are both alkyl, X is O, wherein $A^1$ and $A^2$ are both L-alanine, and wherein n is 4

In certain preferred embodiments, the label compound comprises a biotin moiety and a second reactive moiety that is an alkyne moiety.

In certain preferred embodiments, the sirtuin substrate has the formula:

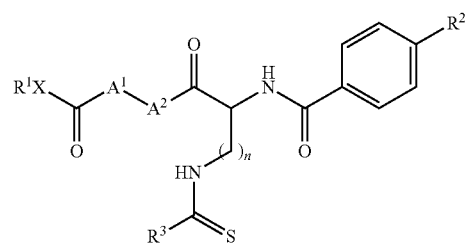

wherein $R^1$ is hydrogen, optionally substituted alkyl or optionally substituted aryl, X is O or $NR^7$, $R^2$ is selected from the group consisting of alkynyl, cycloalkynyl, and alkynylarylalkylcarbonyl, $A^1$ and $A^2$ are the same or different and are amino acids, $R^3$ is alkyl, $R^7$ is hydrogen or alkyl, and n is an integer of 1 to 10.

In a preferred embodiment, $R^1$ and $R^3$ are both alkyl, X is O, wherein $A^1$ and $A^2$ are both L-alanine, and wherein n is 4.

In certain preferred embodiments, the label compound comprises biotin moiety and a second reactive moiety that is an azido moiety.

In certain of any of the above embodiments, the method further comprises the steps of (i') providing a first control mixture comprising (a) the sirtuin substrate comprising a thioamide moiety and a first reactive moiety and (b) NAD+, (ii') adding the sirtuin to the first control mixture to form a second control mixture, (iii') incubating the second control mixture for a period of time, (iv') adding the biotinylated compound comprising a second reactive moiety to the second control mixture to form a third control mixture, wherein the first and second reactive moieties react to form at least one covalent bond between the sirtuin substrate and the biotinylated compound, (v') contacting the third control mixture with a solid phase so as to immobilize components comprising a biotin moiety and to form a control solid phase, (vi') separating uncomplexed components from the control solid phase, (vii') subjecting the control solid phase to conditions to regenerate the sirtuin from the control solid phase and to form a fourth control mixture, and (viii') determining if the sirtuin is present in a decreased amount in the fourth test mixture relative to the fourth control mixture, wherein a decreased amount of the sirtuin in the fourth test mixture relative to the amount of sirtuin that would be observed in the absence of the candidate compound indicates that the candidate compound is an inhibitor of the sirtuin.

In certain embodiments, the sirtuin is two or more sirtuins. Advantageously, the inventive method allows for the simultaneous screening of candidate compounds against two or more sirtuins in a single assay. Advantageously, the inventive method allows for simultaneously determination of compounds that inhibit a sirtuin or sirtuins and the selectivity of the sirtuin inhibition, i.e., the determination of which sirtuin isoform is being inhibited.

The decrease in the amount of sirtuin in the fourth test mixture relative to the amount of sirtuin that would be observed in the absence of the candidate compound can be determined using any suitable technique. For example, the decrease in the amount of sirtuin can be measured by comparison with the amount of sirtuin in the fourth test mixture observed in a control assay, such as an assay performed in the absence of a candidate compound. In some embodiments, the control assay can be performed simultaneously with assay of the candidate compound. In some embodiments, a characteristic associated with the sirtuin can be measured for the control assay and compared with the characteristic observed in the presence of a candidate compound. In an embodiment, the fourth test mixture can be subjected to electrophoresis, such as SDS-PAGE, and the intensity of the band representing the sirtuin can be used to assess the amount of sirtuin present in the fourth test mixture relative to the intensity of the band representing the sirtuin provided by a control assay.

In other embodiments, the method further comprises a step of confirming the inhibitory activity of the candidate compound by independently assaying the inhibitory activity of the candidate compound against a sirtuin.

In an embodiment, the invention provides a compound of the formula:

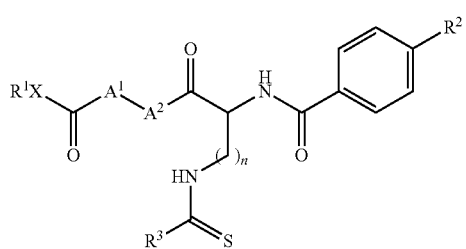

wherein $R^1$ is optionally substituted hydrogen, alkyl or aryl, X is O or $NR^7$, $R^2$ is selected from the group consisting of azido, nitro, alkylazido, arylazido, alkyarylazido, arylalkylazido, alkyloxyamino, aryloxyamino, alkyaryloxyamino, arylalkyloxyamino, alkynyl, cycloalkynyl, and alkynylarylalkylcarbonyl, $A^1$ and $A^2$ are the same or different and are amino acids, $R^3$ is alkyl, and n is an integer of 1 to 10.

In certain embodiments, n is 4.

In certain embodiments, X is O.

In a certain preferred embodiment, $R^2$ is nitro.

In certain preferred embodiments, $R^2$ is selected from the group consisting of azido, alkylazido, arylazido, alkyarylazido, arylalkylazido, alkyloxyamino, aryloxyamino, alkyaryloxyamino, and arylalkyloxyamino.

In certain preferred embodiments, $R^2$ is selected from the group consisting of alkynyl, cycloalkynyl, and alkynylarylalkylcarbonyl.

In a preferred embodiment, $A^1$ and $A^2$ are both alanine.

In certain particular embodiments, the compound is selected from the group consisting of:

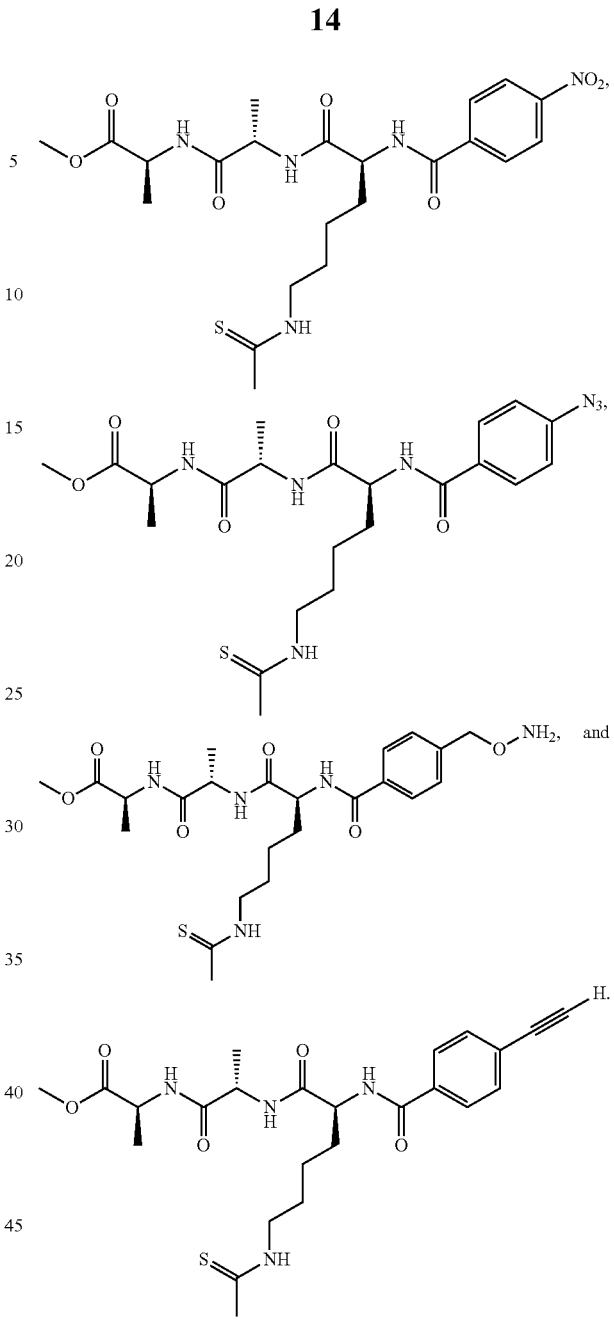

In an embodiment, the invention provides a compound of the formula:

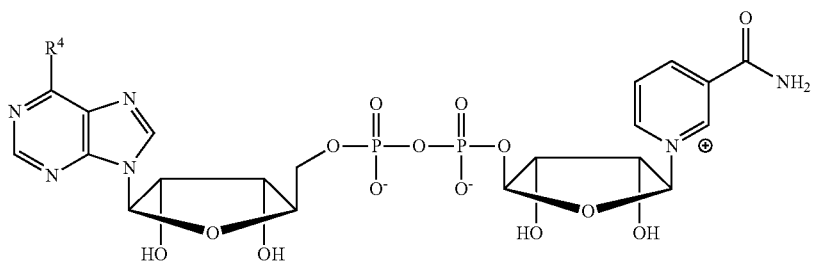

wherein R⁴ is alkyloxyamino, aminooxyethyleneoxyamino, azidooxyethyleneoxyamino, aminooxy(polyethyleneoxy)amino, or azido(polyethyleneoxy)amino.

In particular embodiments, the compound is:

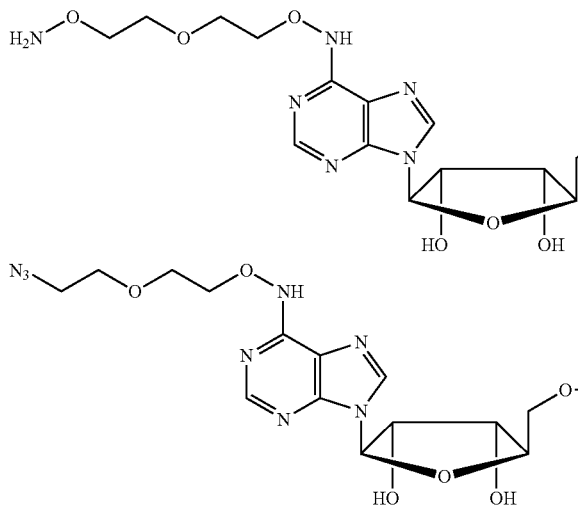 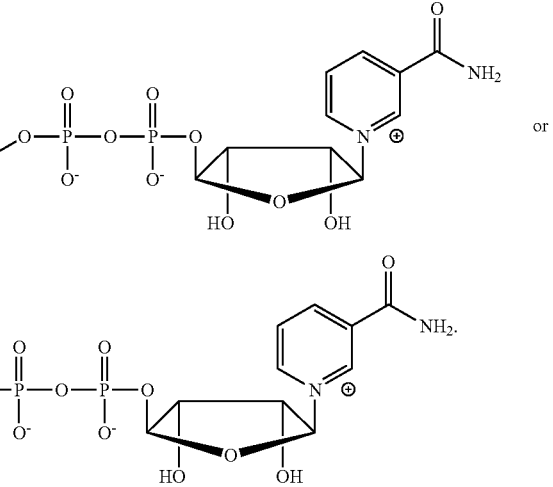

or

Referring now to terminology used generically herein, the term "alkyl" means a straight-chain or branched alkyl substituent containing from, for example, 1 to about 12 carbon atoms, preferably from 1 to about 8 carbon atoms, and more preferably from 1 to 6 carbon atoms. Examples of such substituents include methyl, ethyl, propyl, isopropyl, n-butyl, sec-butyl, isobutyl, tert-butyl, pentyl, isoamyl, hexyl, heptyl, octyl, nonyl, decyl, undecyl, dodecyl, and the like.

The term "alkynyl," as used herein, means a linear alkynyl substituent containing at least one carbon-carbon triple bond and from, for example, 2 to about 12 carbon atoms (branched alkynyls are about 3 to about 12 carbons atoms), preferably from 2 to about 8 carbon atoms (branched alkynyls are preferably from about 3 to about 8 carbon atoms), and more preferably from about 2 to about 6 carbon atoms. Examples of such substituents include ethynyl, propynyl, n-butynyl, pentynyl, hexynyl, and the like.

The term "cycloalkynyl," as used herein, means a cyclic alkyl substituent containing from, for example, about 8 to about 12 carbon atoms, and containing one or more alkynyl groups within the ring structure. The cyclic alkyl groups may be unsubstituted or further substituted with alkyl groups such as methyl groups, ethyl groups, and the like.

The term "halo" or "halogen," as used herein, means a substituent selected from Group VIIA, such as, for example, fluorine, bromine, chlorine, and iodine.

The term "aryl" refers to an unsubstituted or substituted aromatic carbocyclic substituent, as commonly understood in the art, and the term "$C_6$-$C_{10}$ aryl" includes phenyl and naphthyl. It is understood that the term aryl applies to cyclic substituents that are planar and comprise 4n+2 π electrons, according to Hückel's Rule.

The following examples further illustrate the invention but, of course, should not be construed as in any way limiting its scope.

Example 1

This example describes the expression and purification of sirtuin enzymes.

SirT1, SirT2, SirT3, SirT3(118-399), SirT4, SirT5(34-302) and SirT6. The sequences for SirT1, SirT2, SirT3, SirT3 (118-399), SirT4, SirT5(34-302) and SirT6 were cloned into a pSTblue vector by blunt cloning and were subsequently cloned into a pET28a vector (Novagen) containing an N-terminal poly histidine tag. The sequence of the cloned genes was verified by nucleotide sequencing (Genewiz) and checked against the published sequence. The pET28a plasmid containing the sirtuin gene was then transfected into BL21-CodonPlus(DE3)-RIPL Competent cells (Stratagene) and each sirtuin expression was induced by IPTG when the cells were grown to $OD_{600}$ of 0.6~0.7 in LB media. The protein induction conditions were optimized for each sirtuin isoform. Specifically: SirT1 was induced with 100 μM IPTG overnight at room temperature; SirT2 was induced with 500 μM IPTG for 1 hour at 37° C.; SirT3(118-399) was induced with 300 μM IPTG for overnight at room temperature; SirT3, SirT4 and SirT6 were induced with 500 μM IPTG for 1 hour at 37° C.; and SirT5 was induced with 500 μM IPTG for 3 hours at 37° C. Cultures were then pelleted at 4000 rpm for 30 minutes, harvested and lysed by three freeze-thaw cycles. The lysate was incubated with Ni-NTA resin (GBiosciences) at 4° C. for 2 hours and then was washed sequentially with Buffer A (20 mM potassium phosphate, 300 mM NaCl, 10 mM Imidazole) and Buffer B (20 mM potassium phosphate, 300 mM NaCl, 20 mM Imidazole) and protein was eluted with Buffer C (20 mM potassium phosphate, 300 mM NaCl, 200 mM Imidazole). The sirtuin proteins were frozen with 15% glycerol, 2.5 mM DTT and stored at -80° C. Purity was determined by polyacrylamide gel electrophoresis under denaturing conditions using silver staining for visualization of protein. The protein concentration was determined by Bradford Assay.

In the case of SirT5 Ni-NTA, the resin was washed sequentially with Buffer A (50 mM potassium phosphate, 100 mM NaCl, 10 mM imidazole), Buffer B (50 mM potassium phosphate, 100 mM NaCl, 20 mM imidazole) and protein was eluted with Buffer C (50 mM potassium phosphate, 100 mM NaCl, 250 mM imidazole). The protein, with a molecular weight of 33,880 Da, was highly pure, as determined by polyacrylamide gel electrophoresis under denaturing conditions and use of silver staining. In order to obtain even higher purity, the purified protein fractions were run through a DEAE sephadex column and rechecked by polyacrylamide gel electrophoresis.

Example 2

This example demonstrates the synthesis of 6-chloropurine riboside 5'-phosphate.

6-Chloropurine riboside (100 mg, 0.35 mmol) was dissolved in 1.75 mL of trimethyl phosphate. Phosphoryl chloride (160 mg, 1.05 mmol) was dissolved in a mixture of 0.17 mL of trimethylphosphate and 6.3 μL of water. Both solutions were cooled to 0° C., mixed and stirred on a magnetic stirrer at 0° C. After 6 hours, ice was added to quench the reaction and the pH was adjusted to 7 by addition of ammonium hydroxide solution. The crude product was then concentrated and purified on a C18 reverse phase column using water as the mobile phase. The fractions containing desired product were combined and lyophilized to dryness to afford 6-chloropurine riboside 5'-phosphate (96 mg, 0.26 mmol, 75%) as a white solid. $^1$H NMR (D$_2$O, 500 MHz) δ (ppm): 4.20 (m, 2H), 4.42 (m, 1H), 4.55 (t, J=4.6 Hz, 1H), 4.84 (m, 1H), 6.28 (d, J=5.1 Hz, 1H), 8.79 (s, 1H), 8.86 (s, 1H).

Example 3

This example demonstrates the synthesis of $N^6$-(O-[2-(2-aminooxy-ethoxy)-ethyl]-hydroxyamine)-AMP.

O-[2-(2-aminooxy-ethoxy)-ethyl]-hydroxyamine was prepared by the method described in Sadamoto et al., J. Am. Chem. Soc., 126: 3722-3761. A solution of 6-chloropurine riboside 5'-phosphate as described in Example 2 (15 mg, 0.041 mmol) in 0.34 mL of water was treated with a solution of O-[2-(2-aminooxy-ethoxy)-ethyl]-hydroxyamine (56 mg, 0.41 mmol) and triethylamine (14 mg, 0.14 mmol) in 0.33 mL of water at 25° C. and kept overnight. The reaction mixture was concentrated and purified on a C18 reverse phase column using water and methanol as the mobile phase. The desired product was eluted using 10% methanol-90% water as eluent. Appropriate fractions were combined and lyophilized to dryness to afford the title compound (8.6 mg, 0.018 mmol, 45%) as an off-white solid. $^1$H NMR (D$_2$O, 500 MHz) δ (ppm): 3.90 (dt, J=4.2, 18.9 Hz, 4H), 4.14 (m, 2H), 4.28 (dt, J=4.1, 20.6 Hz, 4H), 4.42 (t, J=2.1 Hz, 1H), 4.52 (t, J=4.6 Hz, 1H), 4.82 (m, 1H), 6.18 (d, J=5.0 Hz, 1H), 8.21 (s, 1H), 8.68 (s, 1H).

Example 4

This example demonstrates the synthesis of $N^6$-(O-[2-(2-aminooxy-ethoxy)-ethyl]-hydroxyamine)-NAD$^+$.

A solution of the title product of Example 3 (3 mg, 0.0065 mmol), nicotinamide mononucleotide (4.3 mg, 0.013 mmol) and MgCl$_2$ (14.8 mg, 0.156 mmol) in 1 mL of water was concentrated to dryness. 500 μL of 1.5 M HEPES-NaOH and 500 μL of 5 M EDCI were added to the residue to initiate the coupling reaction. Incubation at 37° C. overnight was followed by dilution with 1 mL of water. The reaction mixture was purified by HPLC on a Waters XBridge™ Prep Shield RP18 column using 0.1% aqueous TFA as eluent at a flow rate of 2 mL/min to afford the title compound ($t_R$=14.5 min, 3.4 mg, 0.0043 mmol, 67%). $^1$H NMR (D$_2$O) δ (ppm): 3.78 (m, 4H), 4.00 (m, 4H), 4.19 (m, 1H), 4.25 (stack, 3H), 4.38 (stack, 2H), 4.46 (m, 1H), 4.52 (stack, 2H), 4.57 (m, 1H), 6.07 (d, J=5.9 Hz, 1H), 6.12 (d, J=5.5 Hz, 1H), 8.21 (s, 1H), 8.23 (dd, J=6.6, 7.8 Hz, 1H), 8.47 (s, 1H), 8.87 (d, J=8.1 Hz, 1H), 9.19 (d, J=6.2 Hz, 1H), 9.37 (s, 1H).

Example 5

N-biotinyl-6-aminohexanal was prepared as described in Allart et al., *Bioconjugate Chem.* 14: 187-194 (2003).

Example 6

Figure 2:
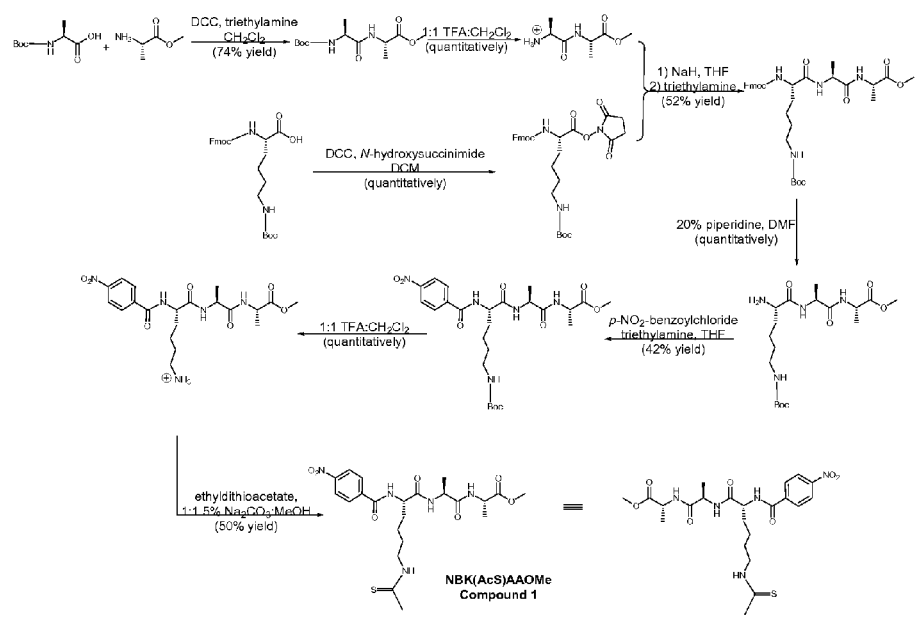
FIG. 2 illustrates a synthesis of p-nitrobenzoyl-(L)-Lys(AcS)-(L)-Ala-(L)-Ala-OMe.

The synthesis of p-nitrobenzoyl-(L)-Lys(AcS)-(L)-Ala-(L)-Ala-OMe is depicted in FIG. 2.

(a) Boc-(L)-Ala-(L)-Ala-OMe was prepared as follows. Boc-(L)-Ala-OH (2.06 g, 10.63 mmol) was dissolved in distilled dichloromethane (5 mL). To the resulting solution was added H$_2$N-(L)-Ala-OMe (0.996 g, 9.67 mmol) in 5 mL of distilled dichloromethane. Dicyclohexylcarbodiimide (abbr. DCC; 2.19 g, 10.63 mmol) was dissolved in 3 mL distilled dichloromethane and added to the solution. Dicyclohexylurea (abbr. DCU) precipitation was noted immediately after DCC addition. Triethylamine (3 mL, 21.52 mmol) and additional distilled dichloromethane (4 mL) were added to the reaction mixture. The reaction proceeded for a total of three hours, when TLC analysis indicated consumption of H$_2$N-(L)-Ala-OMe starting material and formation of a new component. DCU precipitation was promoted by storing the reaction at −20° C. The precipitate was filtered through a Buchner funnel and rinsed with cold dichloromethane. The combined filtrate and rinses were dried under vacuum and purified by Silica chromatography to yield dipeptide Boc-(L)-Ala-(L)-Ala-OMe (2.03 g, 7.14 mmol, 74%). $^1$H-NMR (chloroform-d) δ (ppm): 1.34 (d, J=14.1 Hz, 3H); 1.38 (d, J=14.3 Hz, 3H); 1.40 (s, 9H); 3.73 (s, 3H); 4.14 (s-broad, 1H); 4.55 (quintet, J=14.5 Hz, 1H); 4.97 (s-broad, 1H); 6.59 (s-broad, 1H).

(b) Synthesis of CF$_3$COO$^-$H$_3$N(+-(L)-Ala-(L)-Ala-OMe. Boc-(L)-Ala-(L)-Ala-OMe (0.964 g, 3.30 mmol) was dissolved in distilled dichloromethane (1.7 mL). Trifluoroacetic acid (1.7 mL) and triethylsilane (0.200 mL) were added to the resulting solution. Reaction was allowed to proceed for thirty minutes and then the mixture was concentrated to an oil affording the deprotected dipeptide in quantitative yield. $^1$H-NMR (D$_2$O) δ (ppm): 1.43 (d, J=14.7 Hz, 3H); 1.55 (d, J=14.3 Hz, 3H), 3.76 (s, 3H), 4.09 (q, J=14.2 Hz, 1H); 4.46 (q, J=14.6 Hz, 1H).

(c) Synthesis of Fmoc-(L)-Lys(Boc)O—NHS. Fmoc-(L)-Lys(Boc)OH (1.57 g, 3.35 mmol) and N-hydroxysuccinimide (abbr. NHS; 0.360 mg, 3.21 mmol) was dissolved in distilled dichloromethane (4 mL). To the resulting solution was added a solution of DCC in 4 mL of distilled dichloromethane. Precipitation was noted immediately and reaction was allowed to proceed overnight. Precipitated DCU was removed by filtration and was rinsed with cold dichloromethane. The filtrate and rinses were concentrated under vacuum to yield the activated ester in quantitative yield. $^1$H-NMR (chloroform-d) δ (ppm): 1.36 (s, 9H); 1.44 (m, 4H); 1.90 (m, 2H); 2.80 (s, 4H); 3.12 (m, 2H); 4.21 (t, J=13.7 Hz 1H); 4.41 (m, 2H); 4.69 (m-broad, 2H); 5.52, (s-broad, 1H); 7.29 (t, J=14.7 Hz, 2H); 7.37 (t, J=14.9 Hz, 2H); 7.57 (d, J=14.4 Hz 2H); 7.73 (d, J=15.0 Hz 2H).

(d) Synthesis of Fmoc-(L)-Lys(Boc)-Ala-Ala-OMe. CF$_3$COO$^-$H$_3$N(+)-(L)-Ala-(L)-Ala-OMe (0.780 mg, 2.54 mmol) was dissolved in distilled tetrahydrofuran (abbr. THF; 10 mL) and the resulting solution was treated with NaH (0.067 mg, 2.79 mmol) with cooling using an ice/water bath. A solution of Fmoc-(L)-Lys-(Boc)O—NHS (1.40 g, 2.49 mmol) in distilled THF (5 mL) was added to the reaction mixture. Triethylamine (0.531 mL, 3.81 mmol) was added to the reaction. The reaction was allowed to proceed until consumption of dipeptide starting material was evident (1.5 hours). The crude reaction solution was concentrated under vacuum to dryness and purified by Silica chromatography to obtain the desired tripeptide (0.823 mg, 1.32 mmol, 52%). $^1$H-NMR (chloroform-d) δ (ppm): 1.37 (d, J=13.5 Hz, 6H); 1.41 (s, 9H); 1.48 (m, 2H); 1.67 (m, 2H); 1.81 (m, 2H); 2.68 (m, 2H); 3.72 (s, 3H); 4.15 (s-broad, 1H); 4.18 (t, J=13.9 Hz, 1H); 4.37 (d, J=13.0 Hz 1H); 4.49 (m, 2H); 4.72 (s-broad, 1H); 5.61 (s-broad, 1H); 6.68 (d, J=13.4 Hz, 1H); 7.27 (t, J=14.7 Hz, 2H); 7.37 (t, J=14.8 Hz, 2H); 7.56 (d, J=14.6 Hz, 2H); 7.73 (d, J=15.0 Hz, 2H).

(e) Synthesis of $H_2$N-(L)-Lys(Boc)-(L)-Ala-(L)-Ala-OMe. Procedure 1: Fully protected tripeptide (0.074 mg, 0.131 mmol) was dissolved in dimethylformamide (abbr. DMF, 0.800 mL). Piperidine (0.200 mL) added to the resulting solution. The reaction was allowed to proceed for twenty minutes. The solution was pumped to dryness, resuspended in $H_2$O and washed twice with an equal volume of hexanes. The aqueous layer was lyophilized to yield pure N-terminal deprotected tripeptide in quantitative yield. $^1$H-NMR (chloroform-d): 1.34 (d, J=13.8 Hz, 3H); 1.36 (d, J=14.1 Hz, 3H); 1.39 (s, 9H); 1.50 (m, 4H); 1.83 (m, 2H); 3.10 (m, 2H); 3.34 (d, d, J=8.7, 16.1 Hz, 1H); 3.73 (s, 3H); 4.41 (q, J=14.2 Hz, 1H); 4.52 (q, J=14.5 Hz, 1H); 4.55 (s-broad, 1H); 6.60 (d, J=13.8 Hz, 1H); 7.69 (m, 1H).

Procedure 2: Fully protected tripeptide (0.466 mg, 0.747 mmol) was dissolved in DMF (1.60 mL). Piperidine (0.300 mL) was added to the resulting solution. The reaction was allowed to proceed for thirty minutes. The solution was pumped to dryness, redissolved in DMF and dried again. The DMF evaporation process was repeated a total of four times. The solid residue was redissolved in a minimal volume of dichloromethane and the addition of hexanes to the solution caused precipitation. Additional precipitation was promoted by overnight incubation at −20° C. The mother liquor was removed to yield an oily residue that was washed with cold hexanes. The remaining residue was characterized and compared to the $^1$H-NMR spectra in procedure 1. Pure product was obtained (0.250 mg, 0.622, 88% yield).

Synthesis of para-nitrobenzoyl-(L)-Lys(Boc)-(L)-Ala-(L)-Ala-OMe. $H_2$N-(L)-Lys(Boc)-(L)-Ala-(L)-Ala-OMe (0.0897 mg, 0.223 mmol) was dissolved in distilled THF (5.0 mL) and cooled in an ice/$H_2$O bath. Triethylamine (0.065 mL, 0.279 mmol) was added to the resulting solution. para-nitrobenzoyl chloride (0.051 mg, 0.469 mmol) was added to the reaction mixture. Precipitation was noted immediately. TLC analysis indicated that tripeptide starting material was consumed and a new product had formed at a reaction time of thirty minutes. The reaction mixture was evaporated to dryness and redissolved in d$H_2$O. The aqueous suspension was diluted with ethyl acetate (abbr. EtOAc) and the organic layer was collected. The aqueous layer was extracted three times with EtOAc. The combined organic layers were dried over anhydrous $Na_2SO_4$ and evaporated under vacuum. Silica chromatography was performed to yield pure product para-nitrobenzoyl-(L)-Lys(Boc)-(L)-Ala-(L)-Ala-OMe (0.0513 mg, 0.093 mmol, 42%). $^1$H-NMR (chloroform-d) δ (ppm): 1.37 (s, 9H), 1.40 (d, J=15.3 Hz, 3H); 1.43 (m, 4H); 1.50 (m, 2H) 1.69 (m, 1H); 1.80 (m, 1H); 1.92 (m, 1H); 3.06 (m, 2H); 3.72 (s, 3H); 4.52 (quintet, J=14.4 Hz, 1H); 4.50 (quintet, J=14.4 Hz, 1H); 4.1 (q, J=14.9 Hz, 1H); 4.78 (s-broad, 1H); 6.91 (d, J=14.5 Hz, 1H); 7.08 (d, J=14.9 Hz, 1H); 7.49 (d, J=14.2 Hz, 1H); 8.00 (d, J=16.9 Hz, 2H); 8.24 (d, J=17.4 Hz, 2H).

Synthesis of para-nitrobenzoyl-(L)-Lys($NH_3^+$)-(L)-Ala-(L)-Ala-OMe. para-nitrobenzoyl-(L)-Lys($NH_3^+$)-(L)-Ala-(L)-Ala-OMe (0.0513 g, 0.093 mmol) was dissolved in distilled dichloromethane (0.500 mL). Trifluoroacetic acid (0.500 mL) and triethylsilane (0.100 mL) were added to the resulting solution. Reaction was allowed to proceed for forty minutes and then the reaction mixture was concentrated to an oil affording lysine-deprotected tripeptide in quantitative yield. $^1$H-NMR (MeOD) δ (ppm): 1.40 (t, J=15.3 Hz, 6H); 1.56 (q, J=15.3 Hz, 2H); 1.72 (m, 1H); 1.84 (m, 1H); 1.94 (m, 1H); 2.96 (t, J=14.9 Hz, 2H); 3.71 (s, 3H), 4.39 (q of d, J=4.5, 14.6, 2H); 4.57 (t, J=13.7 Hz 1H); 8.06 (d, J=17.6 Hz 2H); 8.32 (d, J=17.5 Hz, 2H).

Synthesis of para-nitrobenzoyl-(L)-Lys(AcS)-(L)-Ala-(L)-Ala-OMe. (Fatkins 2006) para-nitrobenzoyl-(L)-Lys($NH_3^+$)-(L)-Ala-(L)-Ala-OMe (0.018 mg, 0.0318 mmol) was dissolved in methanol (abbr. MeOH, 1.0 mL) and cooled in an ice/water bath. A 5% $Na_2CO_3$ (0.500 mL) was added dropwise over several minutes to the resulting solution with stirring. Upon complete addition of 5% $Na_2CO_3$, ethyl dithioacetate (0.010 mL, 0.105 mmol) was added dropwise to the solution. The reaction was allowed to proceed for fifty minutes while cooling in the melting ice/water bath. TLC indication of starting tripeptide consumption indicated completion of reaction, at which point 1:1 MeOH:d$H_2$O (1.0 mL) was added to the reaction mixture. MeOH was removed by evaporation under vacuum and the remaining aqueous residue was acidified with 6 N HCl to a pH ~1-2, as indicated by pH paper. The aqueous residue was then extracted four times with dichloromethane and the combined organic layer were washed with brine. The organic fraction was dried over anhydrous $Na_2SO_4$ and concentrated to yield a crude oil. Purification by Silica Chromatography afforded pure thioacetylated tripeptide, para-nitrobenzoyl-(L)-Lys(AcS)-(L)-Ala-(L)-Ala-OMe, compound 3, FIG. 3 (0.098 mg, 0.016 mmol, 50%). $^1$H-NMR (acetone-d6) δ (ppm): 1.31 (d, J=14.4 Hz, 3H); 1.33 (d, J=14.6 Hz, 3H); 1.54 (m, 2H); 1.70 (m, 2H); 1.87 (m, 1H); 1.96 (m, 1H); 2.43 (s, 3H); 3.60 (q, J=13.5 Hz, 2H); 3.67 (s, 1H); 4.40 (q, J=13.7 Hz, 1H); 4.49 (q, J=14.2 Hz, 1H); 4.66 (m, 1H); 7.60 (d, J=14.2 Hz, 1H); 7.70 (d, J=14.5 Hz, 1H); 8.14 (d, J=14.7 Hz, 1H); 8.17 (d, J=17.6 Hz, 2H); 8.32 (d, J=17.6 Hz, 1H).

Synthesis of Fmoc-(L)-Lys(AcS)OH (Fatkins 2006). Fmoc-(L)-Lys($NH_2$)OH (0.750 mg, 2.03 mmol) was suspended in absolute ethanol (abbr. EtOH, 4.0 mL) with cooling in an ice/water bath. 5% $Na_2CO_3$ (4.0 mL) was added dropwise to the suspension with stirring. Ethyldithioacetate (0.250 mL, 2.65 mmol) was added dropwise to the suspension. The reaction was allowed to proceed for three hours and forty minutes and was then diluted with 1:1 EtOH:d$H_2$O (2.0 mL). Ethanol was evaporated using airflow and the residual aqueous component was treated according to the protocol employed for the synthesis of compound 3, FIG. 3 Purification by Silica chromatography using an EtOAc/MeOH gradient containing 1% acetic acid yielded an oily product. The product was redissolved in dichloromethane and was washed with 100 mM HCl. The organic fraction was dried over $Na_2SO_4$ to yield pure thioacetylated lysine (0.402 mg, 0.945 mmol, 46%). $^1$H-NMR (chloroform-d) δ (ppm): 1.46 (m, 2H); 1.70 (m, 3H); 1.92 (m, 1H); 2.49 (s, 3H); 3.60 (m, 2H); 4.20 (t, J=13.7 Hz, 1H); 4.41 (m, 3H); 5.37 (d, J=15.3 Hz, 1H); 7.29 (t, J=14.9 Hz, 2H); 7.38 (t, J=14.8 Hz, 2H); 7.471 (s-broad, 1H); 7.55 (d-broad, 2H); 7.75 (d, J=15.0 Hz, 2H).

Synthesis of Fmoc-Lys(AcS)O—NHS. Fmoc-(L)-Lys (AcS)—OH (0.298 mg, 0.699 mmol) was dissolved in distilled dichloromethane (8.0 mL). NHS (0.0885 mg, 0.770 mmol) was added to the solution with stirring. DCC (0.151 mg, 0.734 mmol) was dissolved in distilled dichloromethane (2.0 mL) and added to the stirring solution. Precipitation was noted within ten minutes of reaction time. The reaction was allowed to proceed for a total time of two hours and then was stored at −20° C. to promote additional DCU precipitation.

DCU was removed by filtration and rinsed as described above. The filtrate and rinses were concentrated under vacuum and the resulting crude solid was purified by Silica chromatography to yield the desired NHS-ester (0.131 mg, 0.250 mmol, 36%). $^1$H-NMR (chloroform-d) δ (ppm): 1.50 (m, 2H); 1.67 (m, 1H); 1.77 (m, 1H); 1.96 (m, 2H); 2.51 (s, 3H); 2.84 (s, 4H); 3.59 (m, 1H); 3.71 (m, 1H); 4.20 (t, J=13.2 Hz, 1H); 4.43 (d, J=13.4 Hz, 2H); 4.777 (q, J=12.4 Hz, 1H); 5.36 (d, J=16.2 Hz, 1H); 7.29 (t, J=14.8 Hz, 2H); 7.38 (t, J=14.9 Hz, 2H); 7.55 (d, J=14.8 Hz, 2H); 7.74 (d, J=15.1 Hz, 2H); 7.78 (s-broad, 1H).

Synthesis of Fmoc-(L)-Lys(AcS)-(L)-Ala-(L)-Ala-OMe. H$_3$N(+)-(L)-Ala-(L)-Ala-OMe (0.068 mg, 0.222 mmol) dissolved in distilled THF (3.0 mL). NaH (0.0075 mg, 0.3125 mmol) was added to the reaction mixture with stirring. The solution was vented to allow for off-gassing. Once off-gassing was no longer observed, Fmoc-(L)-Lys(AcS)O—NHS (0.055 mg, 0.143 mmol) dissolved in distilled THF (3.0 mL) was added to the solution. Triethylamine (0.054 mL, 0.387 mmol) was added to the solution after reaction had proceeded for ten minutes. Precipitation was noted. The reaction was allowed to proceed for 2.5 hours when TLC analysis indicated consumption of the NHS-ester. The reaction was evaporated to dryness and the crude residue was purified by Silica chromatography to yield Fmoc-protected tripeptide (0.070 mg, 0.120 mmol, 84%). $^1$H-NMR (chloroform-d) δ (ppm): 1.35 (d, J=20.6 Hz, 6H); 1.70 (m, 6H); 2.49 (s, 3H); 3.59 (q, J=12.0 Hz, 2H); 3.70 (s, 3H); 4.17 (t, J=13.9 Hz, 1H); 4.23 (q, J=14 Hz, 1H); 4.37 (m, 2H); 4.47 (m, 2H); 5.69 (d, J=15.6 Hz, 1H); 6.73 (d, J=14.4 Hz, 1H); 6.78 (d, J=13.4 Hz, 1H); 7.27 (t, J=14.9 Hz, 2H); 7.37 (t, J=15.1 Hz, 2H); 7.54 (d, J=15.0 Hz, 2H); 7.73 (d, J=15.1 Hz, 2H); 8.11 (s-broad, 1H).

Synthesis of H$_2$N-(L)-Lys(AcS)-(L)-Ala-(L)-Ala-OMe. Fmoc-(L)-Lys(AcS)-(L)-Ala-(L)-Ala-OMe (0.085 mg, 0.146 mmol) was dissolved in DMF (0.800 mL). Piperidine was then added (0.200 mL) and the reaction allowed to proceed until completion. Once complete, the solution was evaporated to dryness and treated according to procedure 2 employed for the synthesis of N-terminal deprotected tripeptide above. The pure product was obtained in 90% yield (0.047 mg, 0.130 mmol). $^1$H-NMR (chloroform-d) δ (ppm): 1.38 (d, J=14.1 Hz, 6H); 1.46 (m, 2H); 1.63 (m; 4H); 2.53 (s, 3H); 3.39 (t-broad, 1H); 4.42 (m, 1H); 4.51 (m, 1H); 6.70, 6.71 (d-broad, J=11.8 Hz, 1H); 7.63 (s-broad, 1H); 7.90 (s-broad; 1H).

Synthesis of para-nitrobenzoyl-(L)-Lys(AcS)-(L)-Ala-(L)-Ala-OMe.

H$_2$N-(L)-Lys(AcS)-(L)-Ala-(L)-Ala-OMe (0.047 mg, 0.130 mmol) was dissolved in distilled THF (5.0 mL) on ice/water bath. Triethylamine (0.038 mL, 0.274) was added to the reaction mixture with stirring. para-nitrobenzoyl chloride (0.027 mg, 0.143 mmol) was added to the reaction and precipitation was noted immediately. The reaction was allowed to proceed for a total time of one and one-half hours and then evaporated to dryness. The crude residue was dissolved in dichloromethane and washed with H$_2$O. The aqueous layer was extracted with dichloromethane three times. The combined organic fractions were dried over Na$_2$SO$_4$, and evaporated to a crude residue. Silica chromatography yielded pure product compound 1, FIG. 2 (0.0051 mg, 0.010 mmol, 10%). $^1$H-NMR (chloroform-d) δ (ppm): 1.39 (d, J=17.5 Hz, 3H); 1.40 (d, J=18.3 Hz, 3H); 1.46 (m, 2H); 1.72 (m, 2H); 1.85 (m, 1H); 1.93 (m, 1H); 2.52 (s, 3H); 3.64 (q, J=12.3 Hz, 2H); 3.74 (s, 3H); 4.50 (octet, J=14.0 Hz, 2H); 4.71 (q, J=14.3 Hz, 1H); 6.56 (d, J=14.7 Hz, 1H); 6.70 (d, J=14.0 Hz, 1H); 7.22 (d, J=15.1 Hz, 1H); 7.97 (d, J=17.4 Hz, 2H); 8.07 (s-broad, 1H); 8.27 (d, J=17.4 Hz, 2H). The relatively low yield of pure product may be accounted for by the fact that a substantial amount of by-product was noted by TLC analysis of reaction. $^1$H-NMR analysis of the isolated product indicated it is peptide and nature and may indicate potential isomerization of the tripeptide during the course of the reaction.

Example 7

This example demonstrates an assay for sirtuin inhibition via thioacetylated peptides. Reactions were performed in 50 mM phosphate buffer pH 7.2 in a volume of 25 μL.

SirT1. A typical reaction containing 300 μM NAD$^+$ and 8.75 μM enzyme was incubated for 30 min with varying concentrations of inhibitor compound 1, FIG. 2 (0 to 100 μM) at 37° C. Deacetylation activity was then initiated with the introduction of 200 mM p53mer to the enzyme reaction and incubation for 60 minutes at 37° C. Reactions were quenched with 8 mL 10% TFA on ice. Quenched samples were subjected to centrifugation and then injected onto HPLC using a Macherey-Nagel Nucleosil C18 column. AADPR, NAD$^+$ and nicotinamide (NAM) peaks were resolved using a gradient of 0 to 10% methanol in 20 mM ammonium acetate. Chromatograms were analyzed at 260 nm.

SirT2. A typical reaction containing 800 μM NAD$^+$ and 5.5 μM enzyme was incubated for 30 min with varying concentrations of inhibitor compound 1, FIG. 2 (0 to 1000 μM) at 37° C. Deacetylation activity was then initiated with the introduction of 500 μM p53mer to the enzyme reaction and incubation for 30 minutes at 37° C. Reactions were quenched with 8 μL 10% TFA on ice. Quenched samples were subjected to centrifugation and then injected onto HPLC using a Macherey-Nagel Nucleosil C18 column. AADPR, NAD$^+$ and nicotinamide (NAM) peaks were resolved using a gradient of 0 to 10% methanol in 20 mM ammonium acetate. Chromatograms were analyzed at 260 nm.

SirT3-full length. A typical reaction containing 800 μM NAD$^+$ and 47 μM enzyme was incubated for 30 min with varying concentrations of inhibitor compound 1 (0 to 500 μM) at 37° C. Deacetylation activity was then initiated with the introduction of 500 μM H3mer to the enzyme reaction and incubation for 90 minutes at 37° C. Reactions were quenched with 8 μL 10% TFA on ice. Quenched samples were subjected to centrifugation and then injected onto HPLC using Macherey-Nagel Nucleosil C18 column. AADPR, NAD$^+$ and nicotinamide (NAM) peaks were resolved using a gradient of 0 to 10% methanol in 20 mM ammonium acetate. Chromatograms were analyzed at 260 nm.

AfSir2. A typical reaction containing 800 μM NAD$^+$ and 12.08 μM enzyme was incubated for 15 min with varying concentrations of inhibitor compound 1 (0 to 1000 μM) at 37° C. Deacetylation activity was then initiated with the introduction of 540 μM NBK(Ac)AAOMe to the enzyme reaction and incubation for 60 minutes at 37° C. Reactions were quenched with 10 μL 10% TFA on ice. Quenched samples were subjected to centrifugation and then injected onto HPLC using Macherey-Nagel Nucleosil C18 column. AADPR, NAD$^+$ and nicotinamide (NAM) peaks were resolved using a gradient of 0 to 10% methanol in 20 mM ammonium acetate. Chromatograms were analyzed at 260 nm.

Validation of N$^6$-(O-[2-(2-aminooxy-ethoxy)-ethyl]-hydroxyamine)-NAD$^+$ as a substrate for SirT1.

Reactions containing 500 μM of N$^6$-(O-[2-(2-aminooxy-ethoxy)-ethyl]-hydroxyamine)-NAD$^+$ 500 μM of p53mer peptide or 250 μM of inhibitor peptide compound 1 or a combination of 500 μM of p53mer and 250 μM of compound 1 in 100 mM phosphate buffer at pH 7.5 were initiated by addition of SirT1 to a final concentration of 10.7 μM. The reactions were incubated at 37° C. for 20 minutes before quenched by addition of 0.1% TFA to pH 2. After centrifugation at 13,000 g for 2 minutes to remove precipitates, reactions were injected on HPLC using a Macherey-Nagel Nucleosil C18 column, $N^6$-(O-[2-(2-aminooxy-ethoxy)-ethyl]-hydroxyamine)-$NAD^+$ and corresponding products were resolved by running a gradient of 0 to 10% methanol in 20 mM ammonium acetate and chromatograms were analyzed at 260 nm.

Example 8

This example demonstrates the avidin binding assay (sirtuin capture assay using $N^6$-(O-[2-(2-aminooxy-ethoxy)-ethyl]-hydroxyamine)-$NAD^+$, NBK(AcS)AAOMe and N-biotinyl-6-aminohexanal).

Reactions were typically performed in 100 mM phosphate buffer pH 7.5 in a total volume of 50 μL. A typical reaction containing 800 μM of $N^6$-(O-[2-(2-aminooxy-ethoxy)-ethyl]-hydroxyamine)-$NAD^+$, 400 μM of inhibitor peptide compound 1 was initiated by addition of enzyme, incubated for 30 min at 37° C. and then adjusted to pH 6 by addition of 100 mM phosphate buffer pH 4.25. N-biotinyl-6-aminohexanal compound was added to a final concentration of 1 mM, the reaction was incubated at 25° C. for 30 minutes before 50 μL of avidin agarose resins were added. The reaction was allowed to incubate at 25° C. for another hour. Supernatant was removed, and the resins were washed with 1 mM $NAD^+$ in 100 mM phosphate buffer (3×100 μL). The resins were boiled in SDS-PAGE sample buffer for 10 minutes and subject to gel electrophoresis for analysis.

Example 9

This example demonstrates the synthesis of 2-(2-(2-bromoethoxy)ethoxy)isoindoline-1,3-dione.

To a solution of N-hydroxyphthalimide (352 mg, 2.16 mmol) in 4 mL of DMF was added 2-bromoethyl ether (500 mg, 2.16 mmol) followed by triethylamine (218 mg, 2.16 mmol), and the resulting solution was stirred at 45° C. overnight. Water was added to quench the reaction, the aqueous layer was extracted with ethyl acetate for 3 times, the combined organic layers were washed with brine and dried over anhydrous $Na_2SO_4$. Solvent was removed under reduced pressure, the crude product was purified by silica gel column chromatography (hexanes: ethyl acetate 2:1) to afford 2-(2-(2-bromoethoxy)ethoxy)isoindoline-1,3-dione (550 mg, 1.75 mmol, 81%) as colorless oil. $^1$H NMR ($CDCl_3$, 500 MHz) δ (ppm): 3.38 (t, J=6.2 Hz, 2H), 3.81 (t, J=6.2 Hz, 2H), 3.87 (t, J=4.1 Hz, 2H), 4.37 (t, J=4.1 Hz, 2H), 7.73 (dd, J=3.0, 5.0 Hz, 2H), 7.82 (dd, J=3.2, 5.0 Hz, 2H).

Example 10

Synthesis of 2-(2-(2-azidoethoxy)ethoxy)isoindoline-1,3-dione.

To 1 mL of DMF/$H_2O$ (v/v=9/1) was added 2-(2-(2-bromoethoxy)ethoxy)isoindoline-1,3-dione (50 mg, 0.17 mmol) and sodium azide (16.6 mg, 0.26 mmol). The mixture was heated to 80° C. overnight. Then it was allowed to cool down to room temperature and was extracted with ethyl acetate for 3 times. The combined organic layers were washed with brine and dried over anhydrous $Na_2SO_4$. Solvent was removed under reduced pressure, the crude product was purified by silica gel column chromatography (hexanes: ethyl acetate 2:1) to afford 2-(2-(2-azidoethoxy)ethoxy)isoindoline-1,3-dione (44 mg, 0.17 mmol, 100%) as colorless oil. $^1$H NMR ($CDCl_3$, 500 MHz) δ (ppm): 3.28 (t, J=4.7 Hz, 2H), 3.64 (t, J=4.8 Hz, 2H), 3.84 (t, J=3.8 Hz, 2H), 4.34 (t, J=3.9 Hz, 2H), 7.71 (dd, J=2.6, 4.7 Hz, 2H), 7.79 (dd, J=3.2, 5.0 Hz, 2H).

Example 11

Synthesis of O-(2-(2-azidoethoxy)ethyl)hydroxylamine.

To a solution of 2-(2-(2-azidoethoxy)ethoxy)isoindoline-1,3-dione (43 mg, 0.17 mmol) in 0.8 mL of methanol was added hydrazine (5.5 mg, 0.17 mmol), and the resulting mixture was allowed to stir at room temperature for 2 h. Solvent was removed under reduced pressure, the crude product was purified by silica gel column chromatography (hexanes: ethyl acetate 1:2) to afford O-(2-(2-azidoethoxy)ethyl)hydroxylamine (15 mg, 0.10 mmol, 60%) as colorless oil. $^1$H NMR ($CDCl_3$, 500 MHz) δ (ppm): 3.38 (t, J=4.8 Hz, 2H), 3.65 (stack, 4H), 3.82 (t, J=4.2 Hz, 2H), 5.49 (s, br, 2H).

Example 12

Synthesis of 6-azido-AMP.

To a solution of 6-chloropurine ribose 5'-phosphate (38 mg, 0.1 mmol) and O-(2-(2-azidoethoxy)ethyl)hydroxylamine (15 mg, 0.1 mmol) in 0.2 mL of water was added triethylamine (30.3 mg, 0.3 mmol). The reaction was stirred at room temperature overnight. Solvent was removed in vacuo and the crude product was purified by HPLC on a Waters XBridge® Prep Shield RP18 column (solvent was 0.1% TFA, compound was eluted at a flow rate of 2 mL/min) to afford 6-azido-AMP ($t_R$=17 min, 19 mg, 0.04 mmol, 40%). $^1$H NMR ($D_2O$, 500 MHz) δ (ppm): 3.51 (t, J=4.7 Hz, 2H), 3.76 (t, J=4.5 Hz, 2H), 3.91 (m, 2H), 4.15 (m, 1H), 4.19 (m, 1H), 4.32 (m, 2H), 4.41 (s, 1H), 4.51 (t, J=4.5 Hz, 1H), 4.74 (m, 1H), 6.17 (d, J=4.7 Hz, 1H), 8.20 (s, 1H), 8.65 (s, 1H); MS (M+1): calcd. 477.12. found 477.40.

Example 13

Synthesis of 6-azido-$NAD^+$.

To a mixture of 6-azido-AMP (2 mg, 0.0043 mmol), nicotinamide mononucleotide (2.9 mg, 0.0086 mmol) and $MgCl_2$ (10.5 mg, 0.052 mmol) were added 172 μL of 1.5 M HEPES-NaOH and 172 μL of 5 M EDCI to initiate the coupling reaction. Incubation at 37° C. for 6 h was followed by dilution with 1 mL of water. The reaction mixture was purified by HPLC on a Waters XBridge® Prep Shield RP18 column (solvent was 0.1% TFA, compound was eluted at a flow rate of 2 mL/min) to afford 6-azido-$NAD^+$ ($t_R$=20 min, 1.1 mg, 0.0013 mmol, 30%). $^1$H NMR ($D_2O$, 500 MHz) δ (ppm): 3.55 (t, J=4.9 Hz, 2H), 3.79 (t, J=4.7 Hz, 2H), 3.94 (m, 2H), 4.32 (stack, 6H), 4.42 (m, 2H), 4.51 (dd, J=2.8, 4.9 Hz, 1H), 4.54 (t, J=4.6 Hz, 1H), 4.61 (t, J=5.2 Hz, 1H), 4.64 (m, 1H), 6.12 (d, J=5.2 Hz, 1H), 6.20 (d, J=5.4 Hz, 1H), 8.13 (s, 1H), 8.31 (t, J=6.6 Hz, 1H), 8.59 (s, 1H), 8.96 (d, J=8.1 Hz, 1H), 9.29 (d, J=6.2 Hz, 1H), 9.45 (s, 1H); MS ($M^+$): calcd. 793.17. found 793.46.

Example 13

Figure 3:
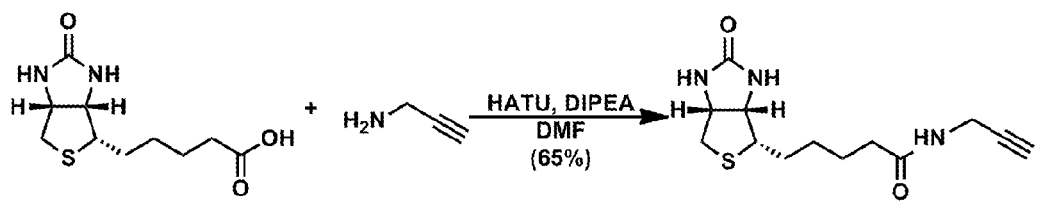
FIG. 3 illustrates a synthesis of an alkynyl biotin label compound.

The synthesis of alkynyl-biotin is depicted in FIG. 3.
HATU (156 mg, 0.41 mmol) was added to a solution of biotin (100 mg, 0.41 mmol), propargylamine (27 mg, 0.49 mmol) and DIPEA (171 mg, 1.23 mmol) in 2 mL of anhydrous DMF. The solution was stirred at room temperature under argon overnight. Solvent was then evaporated under reduced pressure. The crude product was purified by silica gel column chromatography (ethyl acetate: methanol 3:1) to afford alkynyl-biotin (75 mg, 0.27 mmol, 65%) as a off-white solid. $^1$H NMR (CD$_3$OD, 500 MHz) δ (ppm): 1.43 (m, 2H), 1.56 (m, 1H), 1.65 (m, 2H), 1.72 (m, 1H), 2.21 (t, J=7.3 Hz, 2H), 2.56 (s, 1H), 2.69 (d, J=12.8 Hz, 1H), 2.85 (s, 1H), 2.92 (dd, J=4.9, 12.8 Hz, 1H), 2.99 (s, 1H), 3.20 (m, 1H), 3.93 (s, 2H), 4.30 (m, 1H), 4.49 (m, 1H); $^{13}$C NMR (CD$_3$OD, 125 MHz) δ (ppm): 26.8, 29.5, 29.8, 36.6, 41.2, 57.0, 61.7, 63.6, 72.2, 77.7, 80.8, 166.2, 175.8.

Example 14

Figure 4:
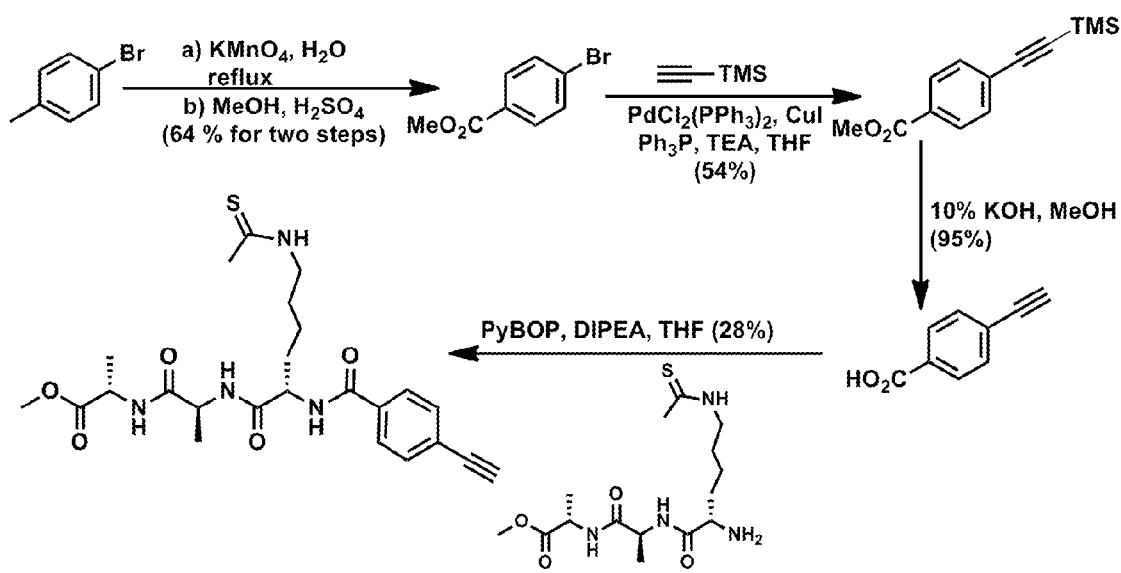
FIG. 4 illustrates a synthesis of $N^\alpha$-4-ethynylbenzoyl-$N^\epsilon$-thioacetyl-lysinyl-alaninyl-alanine methyl ester.

The synthesis of N$^α$-4-ethynylbenzoyl-N$^ε$-thioacetyl-lysinyl-alaninyl-alanine methyl ester is depicted in FIG. 4.

Synthesis of 4-bromobenzoic acid methyl ester.

a) KMnO$_4$ was added in three portions according to the following procedure: KMnO$_4$ (1.515 g, 9.59 mmol) was suspended in water (20 mL). 4-bromotoluene was added dropwise while the reaction stirred vigorously at 60° C. The mixture was allowed to reflux overnight with a loosely placed septum. A second portion of KMnO$_4$ (0.773 g, 4.795 mmol) was added and reaction allowed to continue reflux for 8.5 hr. A final portion of KMnO$_4$ was added and the reaction allowed to reflux for an additional 48 hr, until deemed complete by the consumption of KMnO$_4$ and the formation MnO$_2$. The reaction was filtered under vacuum and precipitate was rinsed with hot water. The aqueous solution was extracted with EtOAc and then acidified to pH 2-3 (as indicated by pH paper). The aqueous layer extracted again with 2× equal volume EtOAc. Pooled organic layers from the second extraction were dried over anhydrous Na$_2$SO$_4$ and evaporated to dryness to afford 4-bromobenzoic acid (0.673 g, 3.3 mmol, 41%). $^1$H-NMR (CD$_2$Cl$_2$, 500 MHz) δ (ppm): 7.63 (d, J=14.1 Hz, 2H); 7.94 (d, J=17.2 Hz, 2H).

b) 4-bromobenzoic acid (1.10 g, 5.39 mmol) was dissolved in MeOH (30 mL). Concentrated H$_2$SO$_4$ (140 mL) was added and the reaction was allowed to reflux for a total of 29 hr. The reaction was quenched with dilute Na$_2$CO$_3$ (15 mL) and equal volume of EtOAc. The solution was diluted with brine to promote phase separation. The aqueous layer was extracted a second time with EtOAc. The combined organic layers were dried over anhydrous Na$_2$SO$_4$ and evaporated to dryness to afford 4-bromobenzoic acid methyl ester (1.124 g, 5.22 mmol, 97%). $^1$H-NMR (CD$_2$Cl$_2$, 500 MHz) δ (ppm): 3.89 (s, 3H); 7.56 (d, J=16.8 Hz, 2H); 7.88 (d, J=16.8 Hz, 2H).

Synthesis of 4-(trimethylsilyl)ethynyl-benzoic acid methyl ester.

4-Bromobenzoic acid methyl ester (1.124 g, 5.22 mmol), PdCl$_2$(PPh$_3$)$_2$ (192 mg, 27.4 mmol), and PPh$_3$ (37 mg, 14.1 mmol) were suspended in THF (25.0 mL). Ethynyltrimethylsilane (1.14 mL, 8.1 mmol) and Et$_3$N (1.14 mL, 7.8 mmol) were added and the reaction was allowed to stir for 20 min. CuI (14 mg, 0.075 mmol) was added and the reaction color changed from orange to red. Reaction was allowed to proceed overnight. After overnight reaction, the solution was brown in color and TLC analysis indicated the reaction was complete. The reaction mixture was concentrated to a brown residue, redissolved in DCM and filtered through Celite. The filtrate and rinses were evaporated to dryness and purification via Silica in 15:1 cyclohexane: EtOAc afforded 4-(trimethylsilyl)ethynyl-benzoic acid methyl ester (656 mg, 2.82 mmol, 54%) as an orange solid. H-NMR (CD$_3$Cl, 500 MHz) δ (ppm): 0.239 (s, 9H); 3.89 (s, 3H); 7.49 (d, J=16.84 Hz, 2H); 7.94 (d, J=16.4 Hz, 2H).

Synthesis of 4-ethynylbenzoic acid.

4-(Trimethylsilyl)ethynyl-benzoic acid methyl ester (714 mg, 3.07 mmol) was dissolved in 4% KOH:MeOH (w:v, 30 mL) and allowed to reflux overnight. The reaction was quenched with 6N HCl to pH 2-3 (as indicated by pH paper) and extracted 2× with EtOAc. The combined organic layers were dried over anhydrous Na$_2$SO$_4$ and evaporated to afford 4-ethynylbenzoic acid (427 mg, 2.92 mmol, 95%) as a brown solid. H-NMR (d$_6$-acetone, 500 MHz) δ (ppm): 7.62 (d, J=16.2 Hz, 2H); 8.03 (d, J=16.3 Hz, 2H).

Synthesis of N$^α$-4-ethynylbenzoyl-N$^ε$-thioacetyl-lysinyl-alaninyl-alanine methyl ester.

Tripeptide H$_2$NK(AcS)AAOMe (26 mg, 0.072 mmol) was dissolved in THF (2.0 mL). DIPEA (25 mL, 0.144 mmol) was added to the solution. PyBOP (41 mg, 0.079 mmol) and 4-ethynylbenzoic acid (12 mg, 0.079 mmol) were added simultaneously to the solution. At 30 min the reaction appeared yellow in color and TLC analysis indicated consumption of starting material. The reaction mixture was evaporated to a yellow residue and purification by Silica in EtOAc yielded N$^α$-4-ethynylbenzoyl-N$^ε$-thioacetyl-lysinyl-alaninyl-alanine methyl ester (10.1 mg, 0.0206 mmol, 28%). $^1$H-NMR (d$_6$-acetone, 500 MHz) δ (ppm): 1.32 (d, J=14.2 Hz, 3H); 1.34 (d, J=14.6 Hz, 3H); 1.53 (m, 2H); 1.68 (m, 2H); 1.88 (m, 1H); 1.95 (m, 1H); 2.43 (s, 3H); 3.60 (q, J=13.6 Hz, 2H); 3.66 (s, 3H); 4.40 (qt, J=14.6 Hz, 1H); 4.48 (qt, J=14.3 Hz, 1H); 4.61 (m, 1H); 7.57 (d, J=16.7 Hz, 2H); 7.61 (d, J=14.3 Hz, 1H); 7.71 (d, J=14.6 Hz, 1H); 7.94 (d-broad, 3H); 9.15 (s, 1H).

Example 15

Figure 5:
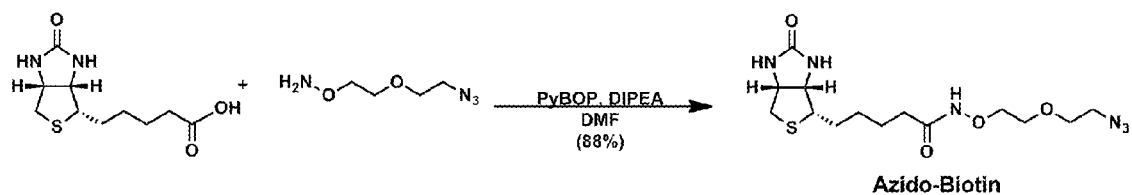
FIG. 5 illustrates a synthesis of an azido biotin label compound.

The synthesis of azido-biotin is depicted in FIG. 5.

To a solution of O-(2-(2-azidoethoxy)ethyl)hydroxylamine (10 mg, 0.068 mmol), biotin (225 mg, 0.103 mmol) and DIPEA (29 mg, 0.206 mmol) in 0.8 mL of DMF was added PyBOP (54 mg, 0.103 mmol). The reaction was allowed to stir at room temperature for 2 h. Solvent was then removed in vacuo, and the crude product was purified by silica gel column chromatography (ethyl acetate: methanol 4:1) to afford azido-biotin (22 mg, 0.059 mmol, 88%) as a pale yellow solid. $^1$H NMR (CD$_3$OD, 500 MHz) δ (ppm): 1.35 (m, 1H), 1.43 (m, 2H), 1.68 (stack, 4H), 2.11 (t, J=7.3 Hz, 2H), 2.70 (d, J=12.8 Hz, 1H), 2.92 (dd, J=5.0, 12.8 Hz, 1H), 3.20 (m, 1H), 3.43 (m, 2H), 3.67 (m, 2H), 3.72 (m, 2H), 3.98 (m, 2H), 4.30 (m, 1H), 4.48 (m, 1H).

Example 16

Figure 14:
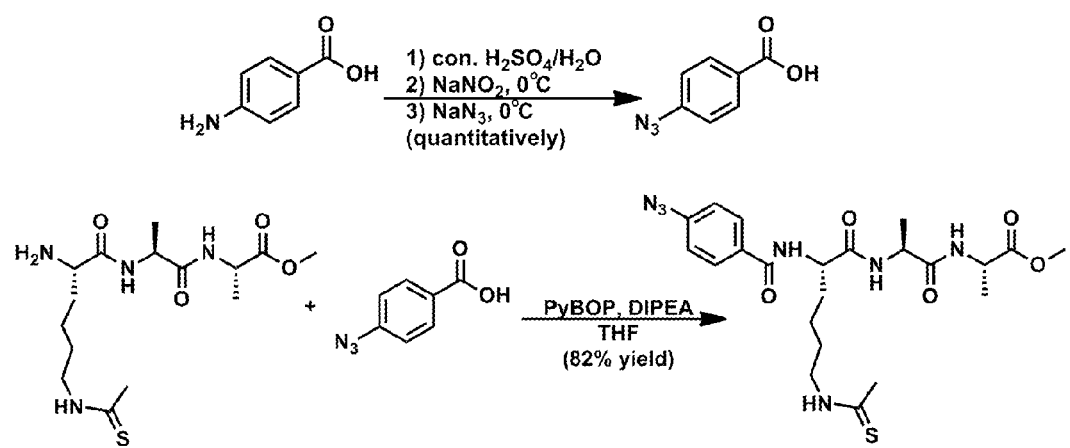
FIG. 14 illustrates a synthesis of $N^\alpha$-4-azidobenzoyl-$N^\epsilon$-thioacetyl-lysinyl-alaninyl-alanine methyl ester.

A synthesis of N$^α$-4-azidobenzoyl-N$^ε$-thioacetyl-lysinyl-alaninyl-alanine methyl ester is depicted in FIG. 14.

Synthesis of 4-azidobenzoic acid.

4-aminobenzoic acid (500 mg, 3.65 mmol) was dissolved in 2.5 mL of water and concentrated sulfuric acid (98%, 0.75 mL) and additional water (0.75 mL) were added. The suspension was cooled to 0° C. and a solution of NaNO$_2$ (265 mg, 3.84 mmol) in 0.75 mL of water was added under constant stirring. Sodium azide (293 mg, 4.5 mmol) was added to the brown solution. After additional 15 min of stirring at 0° C. the precipitate was filtered and washed several times with water. The solid was dried to afford 4-azidobenzoic acid (594 mg, 3.64 mmol, 100%) as a white solid. $^1$H NMR (CD$_3$OD, 500 MHz) δ (ppm): 7.13 (dd, J=1.9, 8.6 Hz, 2H), 8.02 (dd, J=1.9, 8.6 Hz, 2H).

Synthesis of N$^α$-4-azidobenzoyl-N$^ε$-thioacetyl-lysinyl-alaninyl-alanine methyl ester.

To a solution of N$^ε$-thioacetyl-lysinyl-alaninyl-alanine methyl ester (50 mg, 0.14 mmol) in 0.8 mL of THF was added a solution of 4-azidobenzoic acid (35 mg, 0.21 mmol) in 0.8 mL of THF. PyBOP (109 mg, 0.21 mmol) and DIPEA (59 mg, 0.42 mmol) were introduced into the reaction mixture. The reaction was stirred at room temperature for 6 h, and then solvent was removed under reduced pressure. Silica gel column chromatography (ethyl acetate: hexanes 10:1) afforded $N^\alpha$-4-azidobenzoyl-$N^\epsilon$-thioacetyl-lysinyl-alaninyl-alanine methyl ester (58 mg, 0.115 mmol, 82%) as a pale yellow solid. $^1$H NMR (CD$_2$Cl$_2$, 500 MHz) δ (ppm): 1.39 (s, 3H), 1.40 (s, 3H), 1.47 (m, 2H), 1.67 (m, 2H), 1.88 (m, 2H), 2.87 (s, 3H), 3.57 (m, 2H), 3.68 (s, 3H), 4.41 (m, 1H), 4.46 (m, 1H), 4.64 (m, 1H), 7.05 (d, J=8.6 Hz, 2H), 7.20 (d, J=7.2 Hz, 1H), 7.36 (d, J=6.8 Hz, 1H), 7.44 (d, J=7.0 Hz, 1H), 7.86 (d, J=8.6 Hz, 2H), 8.32 (m, 1H).

Example 17

Sirtuin Capture Assay Using 6-Azido-NAD$^+$, NBK(AcS) AAOMe and Alkynyl-Biotin.

Figure 6:
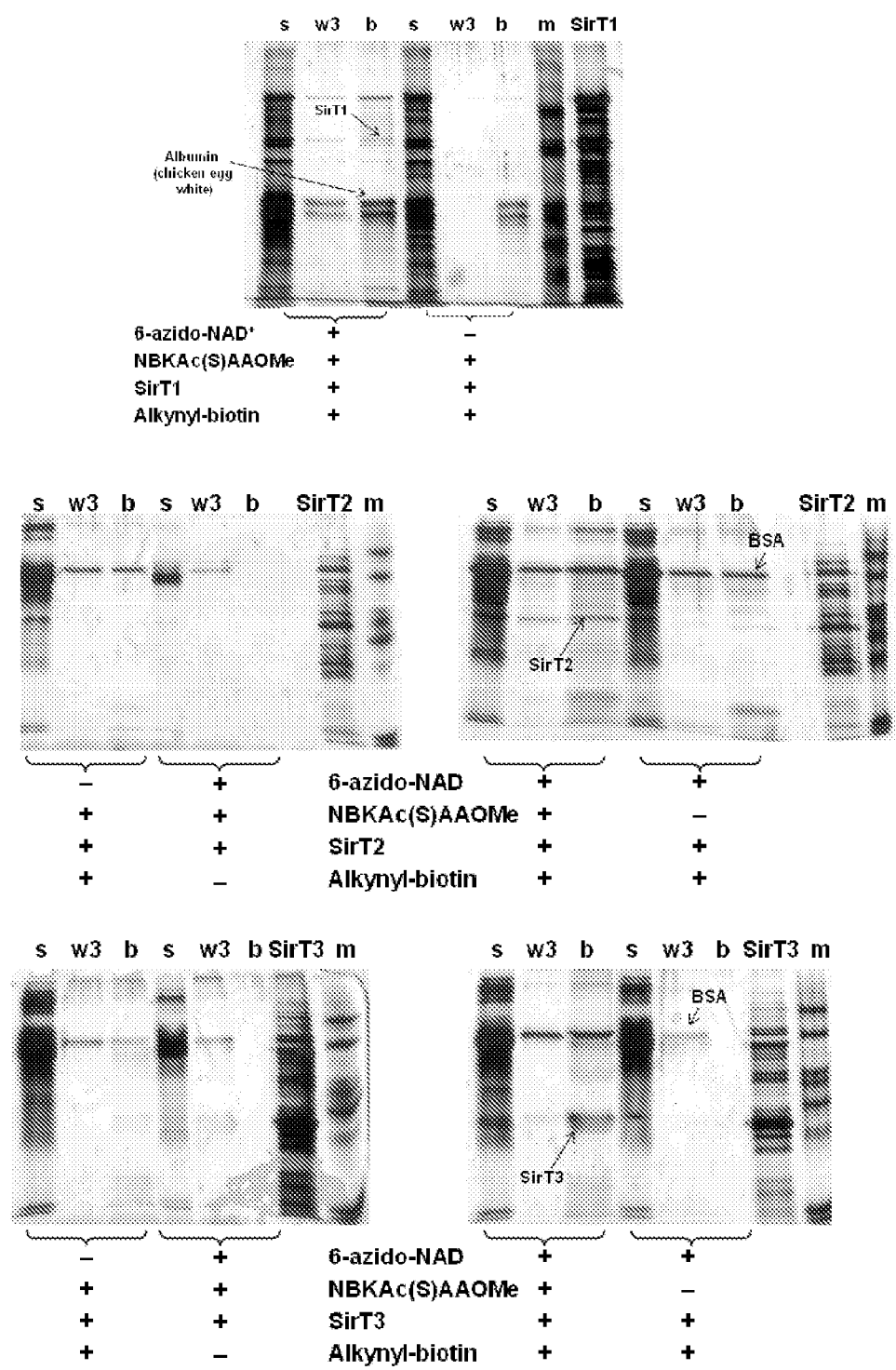
FIG. 6 illustrates SDS-PAGE results for sirtuin capture by 6-azido-$NAD^+$, NBK(AcS)AAOMe, and alkynyl-biotin.

A typical reaction was performed in 100 mM phosphate buffer pH 7.5 in a total volume of 50 μL. Each reaction contained 100 μM of 6-azido-NAD$^+$ and 200 μM of NBK (AcS)AAOMe (compound 1). Three control experiments were run at the same time: the first one contained 100 μM of 6-azido-NAD$^+$ only; the second control sample contained 200 μM of NBK(AcS)AAOMe only; and the third control had both 100 μM of 6-azido-NAD$^+$ and 200 μM of NBK(AcS) AAOMe. Reactions were initiated by addition of enzymes with final concentrations: 5.6 μM for SirT1, 6.7 μM for SirT2, 9.8 μM for SirT3 and 7.2 μM for SirT5. Reactions were incubated at 37° C. for 30 min and then alkynyl-biotin was added to each sample (except for the third control sample which received same volume of vehicle) to a final concentration of 100 μM followed by 3 μL of freshly premixed click chemistry cocktail: CuSO$_4$ (final concentration 1 mM), tris [(1-benzyl-1H-1,2,3-triazol-4-yl)methyl]amine (TBTA, final concentration 600 μM) and tris(2-carboxyethyl)phosphine hydrochloride (TCEP, final concentration 2 mM). The samples were incubated at room temperature for 30 min. Then, 50 μL streptavidin beads (pretreated with either 1 mM albumin from chicken egg white (for SirT1) or 1 mM of BSA (for other sirtuins)) were added to each sample and the incubation were continued at room temperature for 1 h. After removal of the supernatant, the beads were washed with 1 mM NAD$^+$ in 100 mM phosphate buffer (3×100 μL). The beads were boiled in SDS-PAGE sample buffer for 10 min and subjected to SDS-PAGE gel for analysis. The gels were visualized using silver stain protocol. Gels for SirT1, SirT2, SirT3 and SirT5 are shown in FIG. 6.

Example 18

Sirtuin Capture Assay Using NAD$^+$, Alkynyl-thiotripeptide and Azido-biotin.

Figure 7:
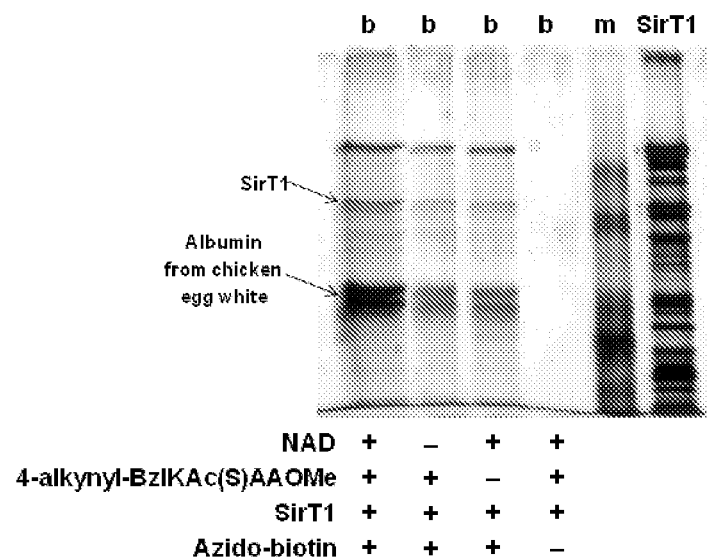
FIG. 7 illustrates SDS-PAGE results for sirtuin capture by $NAD^+$, alkynyl thiotripeptide, and azido-biotin.
Figure 7:
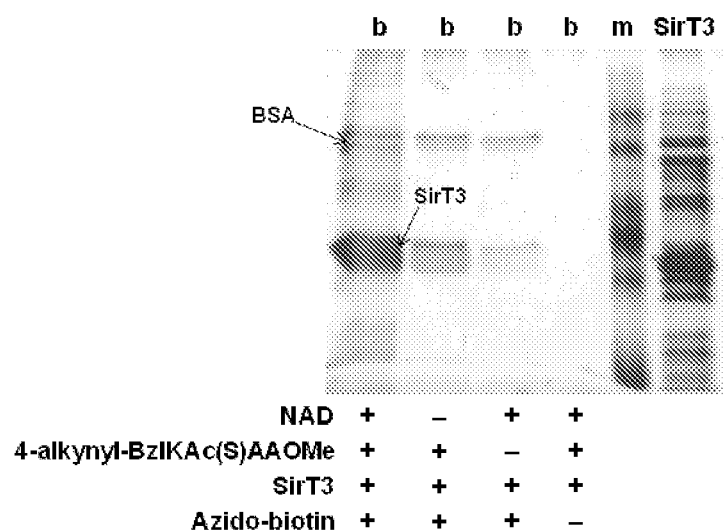

A typical reaction was performed in 100 mM phosphate buffer pH 7.5 in a total volume of 50 μL. Each reaction contained 100 μM of NAD$^+$ and 200 μM of 4-alkynyl-BzlK (AcS)AAOMe. Three control experiments were run at the same time: the first one contained 100 μM of NAD$^+$ only; the second control sample contained 200 μM of 4-alkynyl-BzlK (AcS)AAOMe only; and the third control had both 100 μM of NAD$^+$ and 200 μM of 4-alkynyl-BzlK(AcS)AAOMe. Reactions were initiated by addition of enzymes with final concentrations: 5.6 μM for SirT1, 9.8 μM for SirT3. For sirtuin mixture samples, enzyme concentrations were 5 μM for SirT1, 5.1 μM for SirT2, 4.9 μM for SirT3, 5.04 μM for SirT5 and 5.1 μM for SirT6. Reactions were incubated at 37° C. for 30 min and then azido-biotin was added to each sample (except for the third control sample which received same volume of vehicle) to a final concentration of 100 μM followed by 3 μL of freshly premixed click chemistry cocktail: CuSO$_4$ (final concentration 1 mM), tris[(1-benzyl-1H-1,2,3-triazol-4-yl) methyl]amine (TBTA, final concentration 600 μM) and tris (2-carboxyethyl)phosphine hydrochloride (TCEP, final concentration 2 mM). The samples were incubated at room temperature for 30 min. Then, 50 μL streptavidin beads (pretreated with either 1 mM albumin from chicken egg white (for SirT1) or 1 mM of BSA (for other sirtuins)) were added to each sample and the incubation were continued at room temperature for 1 h. After removal of the supernatant, the beads were washed with 1 mM NAD$^+$ in 100 mM phosphate buffer (3×100 4). The beads were boiled in SDS-PAGE sample buffer for 10 min and subjected to SDS-PAGE gel for analysis. The gels were visualized using silver stain protocol. Gels for SirT1, SirT3 and sirtuin mixture are shown in FIG. 7.

Example 19

Sirtuin Capture Assay Using NAD$^+$, Alkynyl-thiotripeptide and Azido-Dye

A typical reaction was performed in 100 mM phosphate buffer pH 7.5 in a total volume of 50 μL. Each reaction contained 500 μM of NAD$^+$ and 200 μM of 4-alkynyl-BzlK (AcS)AAOMe. Three control experiments were run at the same time: the first one contained 500 μM of NAD$^+$ only; the second control sample contained 200 μM of 4-alkynyl-BzlK (AcS)AAOMe only; and the third control had both 500 μM of NAD$^+$ and 200 μM of 4-alkynyl-BzlK(AcS)AAOMe. Reactions were initiated by addition of enzymes with final concentration: 9.8 μM for SirT3 (except for the third control sample which received same volume of vehicle). Reactions were incubated at 37° C. for 30 min and then azide-fluor 545 (Click Chemistry Tools, LLC) was added to each sample to a final concentration of 200 μM followed by 3 μL of freshly premixed click chemistry cocktail: CuSO$_4$ (final concentration 1 mM), tris[(1-benzyl-1H-1,2,3-triazol-4-yl)methyl] amine (TBTA, final concentration 600 μM) and tris(2-carboxyethyl)phosphine hydrochloride (TCEP, final concentration 2 mM). The samples were incubated at room temperature for 30 min. The samples were then subjected to mini quick spin DNA columns (Roche Diagnostics) and eluents were visualized under UV. Tubes containing eluents from sample are shown in FIG. 8.

Example 20

Sirtuin Capture Assay Using NAD$^+$, Azido-thiotripeptide and Alkynyl-biotin.

Figure 9:
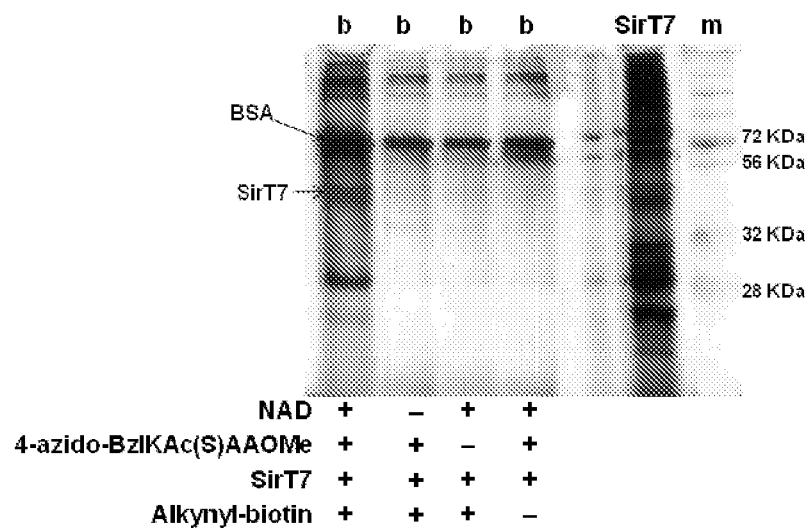
FIG. 9 illustrates SDS-PAGE results for sirtuin capture by $NAD^+$, azido thiotripeptide, and alkynyl-biotin.

A typical reaction was performed in 100 mM phosphate buffer pH 7.5 in a total volume of 50 μL. Each reaction contained 100 μM of NAD$^+$ and 200 μM of 4-azido-BzlK (AcS)AAOMe. Three control experiments were run at the same time: the first one contained 100 μM of NAD$^+$ only; the second control sample contained 200 μM of 4-azido-BzlK (AcS)AAOMe only; and the third control had both 100 μM of NAD$^+$ and 200 μM of 4-azido-BzlK(AcS)AAOMe. Reactions were initiated by addition of enzymes with final concentrations: 20 μM for SirT7. Reactions were incubated at 37° C. for 30 min and then alkynyl-biotin was added to each sample (except for the third control sample which received same volume of vehicle) to a final concentration of 200 μM followed by 3 μL of freshly premixed click chemistry cocktail: CuSO$_4$ (final concentration 1 mM), tris[(1-benzyl-1H-1, 2,3-triazol-4-yl)methyl]amine (TBTA, final concentration 600 μM) and tris(2-carboxyethyl)phosphine hydrochloride (TCEP, final concentration 2 mM). The samples were incubated at room temperature for 30 min. Then, 50 μL streptavidin beads (pretreated with 1 mM of BSA) were added to each sample and the incubation were continued at room temperature for 1 h. After removal of the supernatant, the beads were washed with 1 mM $NAD^+$ in 100 mM phosphate buffer (3×100 4). The beads were boiled in SDS-PAGE sample buffer for 10 min and subjected to SDS-PAGE gel for analysis. The gels were visualized using silver stain protocol. Gel for SirT7 is shown in FIG. 9.

Example 21

Sirtuin Inhibitor Screening Assay Using $NAD^+$, Azidothiotripeptide and Alkynyl-Biotin.

The key criterion for our pulldown technology is the formation of a stalled thioimidate complex with a cross-linkable moiety at the active site on sirtuins. If the presence of a sirtuin inhibitor can interrupt thioimidate formation, there will be less or no sirtuin can be harvested later on. Hence our technology should enable screening for potential sirtuin inhibitors.

Figure 10:
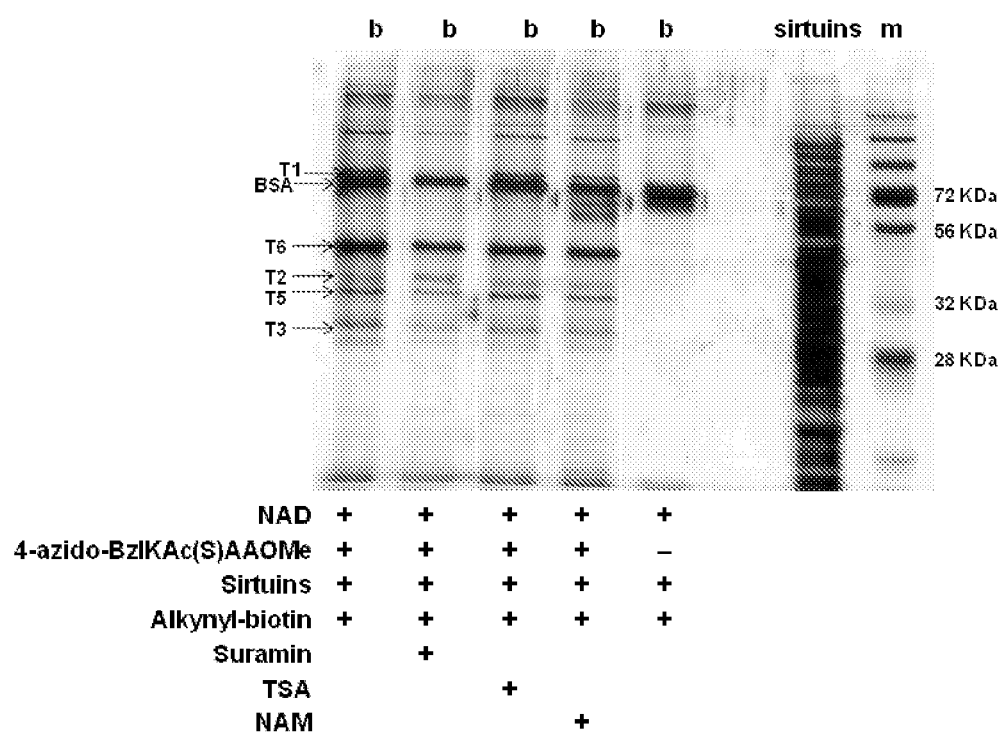
FIG. 10 illustrates SDS-PAGE results for sirtuin inhibitor screening.
Figure 11:
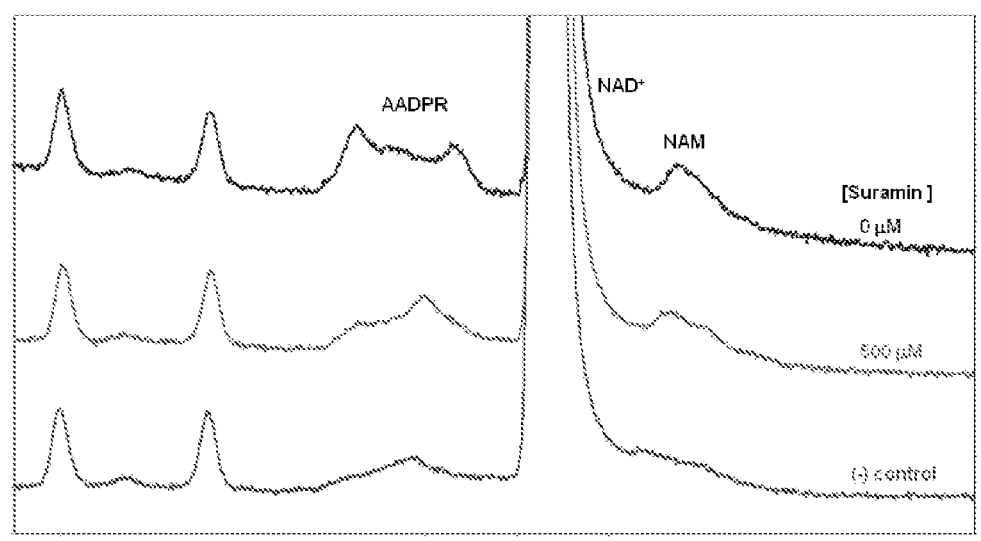
FIG. 11 illustrates HPLC chromatograms of enzyme reactions of SirT1 with p53mer in the presence and absence of suramin.

Pulldown assay: a typical reaction was performed in 100 mM phosphate buffer pH 7.5 in a total volume of 100 μL. Each reaction contained 500 μM of $NAD^+$, 200 μM of 4-azido-BzlK(AcS)AAOMe, and various concentrations of potential inhibitors. One control experiment which contained 500 μM of $NAD^+$ only were run at the same time. Reactions were initiated by addition of enzymes with final concentrations: 5 μM for SirT1, 3.4 μM for SirT2, 4.9 μM for SirT3, 5.04 μM for SirT5 and 5.35 μM for SirT6. Reactions were incubated at 37° C. for 30 min and then alkynyl-biotin was added to each sample to a final concentration of 500 μM followed by 3 μL of freshly premixed click chemistry cocktail: $CuSO_4$ (final concentration 1 mM), tris[(1-benzyl-1H-1,2,3-triazol-4-yl)methyl]amine (TBTA, final concentration 600 μM) and tris(2-carboxyethyl)phosphine hydrochloride (TCEP, final concentration 2 mM). The samples were incubated at room temperature for 30 min. Then, 50 μL streptavidin beads (pretreated with 1 mM of BSA) were added to each sample and the incubation were continued at room temperature for 1 h. After removal of the supernatant, the beads were washed with 1 mM $NAD^+$ in 100 mM phosphate buffer (3×100 μL). The beads were boiled in SDS-PAGE sample buffer for 10 min and subjected to SDS-PAGE gel for analysis. The gels were visualized using silver stain protocol. Gel for sirtuin mixture with different inhibitor candidates are shown in FIG. 10. In this experiment the concentrations for inhibitors were 500 μM for suramin, 20 μM for trichostatin A (TSA), and 15 mM for nicotinamide (NAM). Suramin is a known sirtuin inhibitor with $IC_{50}$ in the low micromolar range. Indeed we observed less SirT1, SirT3 and SirT5 being captured by standard pulldown assay. And these inhibitions were further confirmed by HPLC assay (FIG. 11). On the other hand, TSA, a known class I and class II HDAC inhibitor, showed no effects on class III HDACs (sirtuins) as expected.

HPLC assay: reactions were performed in 100 mM phosphate buffer pH 7.5 in a total volume of 50 μL. Each reaction contained 500 μM of $NAD^+$, 300 μM of p53mer and various concentrations of suramin. Reactions were initiated by addition of SirT1 to a final concentration of 3 μM. A negative control which contained 500 μM of $NAD^+$ and 300 μM of p53mer, but was quenched by addition of TFA before the addition of enzyme was run at the same time. The reactions were incubated at 37° C. for 20 min before being quenched by 8 of 10% TFA. The samples were then injected on an HPLC fitted to a Macherey-Nagel Nucleosil C18 column. AADPR, $NAD^+$ and NAM peaks were resolved using a gradient of 0 to 10% methanol in 20 mM ammonium acetate. Chromatograms were analyzed at 260 nm. HPLC chromatograms of activities of SirT1 with or without suramin are shown in FIG. 11.

Example 22

Assay for Quantifying Active Sirtuins

Figure 12:
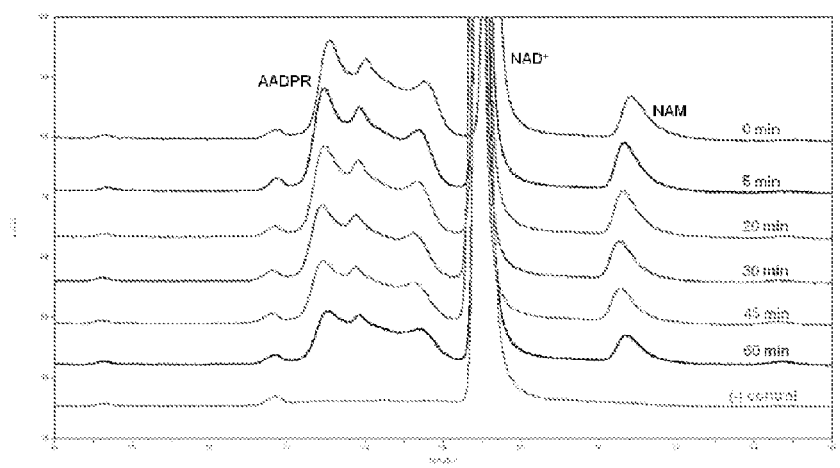
FIG. 12 illustrates HPLC chromatograms of activities of different aged SirT2 samples and the quantification of SirT2 activity.
Figure 12:
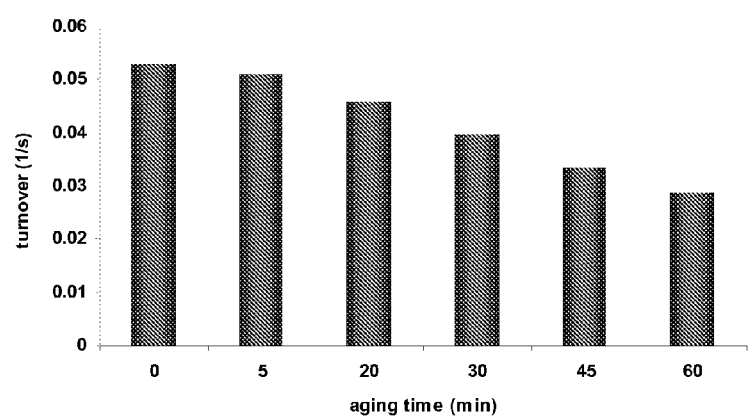

HPLC assay: reactions were performed in 100 mM phosphate buffer pH 7.5 in a total volume of 50 μL. Each reaction contained 300 μM of $NAD^+$ and 300 μM of H3mer. Reactions were initiated by addition of SirT2 that have been incubated at 45° C. for 0, 5, 20, 30, 45 and 60 min to a final concentration of 4.32 μM. A negative control which contained 300 μM of $NAD^+$ and 300 μM of H3mer, but was quenched by addition of TFA before the addition of enzyme was run at the same time. The reactions were incubated at 37° C. for 10 min before being quenched by 8 μL of 10% TFA. The samples were then injected on an HPLC fitted to a Macherey-Nagel Nucleosil C18 column. AADPR, $NAD^+$ and NAM peaks were resolved using a gradient of 0 to 10% methanol in 20 mM ammonium acetate. Chromatograms were analyzed at 260 nm. Reactions were quantified by integrating areas of peaks corresponding to $NAD^+$ and deacetylation product AADPR. HPLC chromatograms of activities of different aged SirT2 samples are shown in FIG. 12 along with the quantification of SirT2 activity. These results were further confirmed by pulldown assay.

Figure 13:
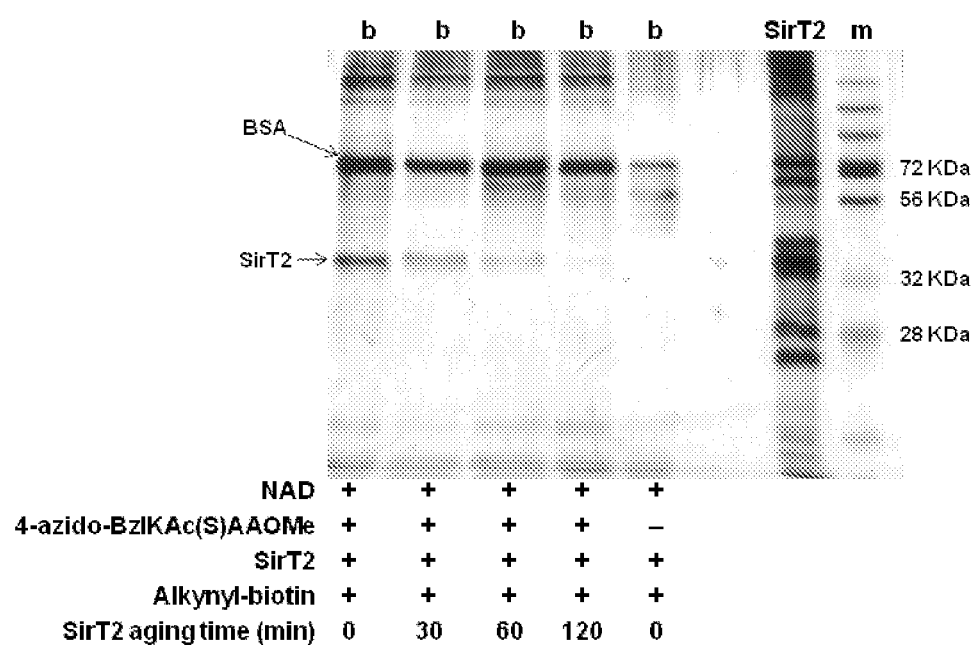
FIG. 13 illustrates SDS-PAGE results for quantifying active SirT2.

Pulldown assay: A typical reaction was performed in 100 mM phosphate buffer pH 7.5 in a total volume of 50 μL. Each reaction contained 500 μM of $NAD^+$ and 400 μM of 4-azido-BzlK(AcS)AAOMe, one control experiment contained 500 μM of $NAD^+$ only was run at the same time. Reactions were initiated by addition of SirT2 that have been incubated at 45° C. for 0, 5, 20, 30, 45 and 60 min to a final concentration of 4.32 μM. Reactions were incubated at 37° C. for 30 min and then alkynyl-biotin was added to each sample to a final concentration of 500 μM followed by 3 μL of freshly premixed click chemistry cocktail: $CuSO_4$ (final concentration 1 mM), tris[(1-benzyl-1H-1,2,3-triazol-4-yl)methyl]amine (TBTA, final concentration 600 μM) and tris(2-carboxyethyl)phosphine hydrochloride (TCEP, final concentration 2 mM). The samples were incubated at room temperature for 30 min. Then, 50 μL streptavidin beads (pretreated with 1 mM of BSA) were added to each sample and the incubation were continued at room temperature for 1 h. After removal of the supernatant, the beads were washed with 1 mM $NAD^+$ in 100 mM phosphate buffer (3×100 μL). The beads were boiled in SDS-PAGE sample buffer for 10 min and subjected to SDS-PAGE gel for analysis. The gels were visualized using silver stain protocol. Gel for SirT2 is shown in FIG. 13.

All references, including publications, patent applications, and patents, cited herein are hereby incorporated by reference to the same extent as if each reference were individually and specifically indicated to be incorporated by reference and were set forth in its entirety herein.

The use of the terms "a" and "an" and "the" and similar referents in the context of describing the invention (especially in the context of the following claims) are to be construed to cover both the singular and the plural, unless otherwise indicated herein or clearly contradicted by context. The terms "comprising," "having," "including," and "containing" are to be construed as open-ended terms (i.e., meaning "including, but not limited to,") unless otherwise noted. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

Preferred embodiments of this invention are described herein, including the best mode known to the inventors for carrying out the invention. Variations of those preferred embodiments may become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

The invention claimed is:

1. A method of preparing a sirtuin complex, which method comprises:

(i) providing a first component which is a sirtuin substrate having the formula:

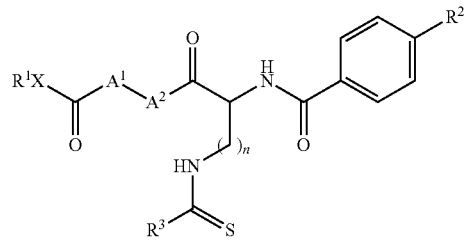

wherein $R^1$ is hydrogen, optionally substituted alkyl or optionally substituted aryl, X is O or $NR^7$, $R^2$ is selected from azido, nitro, alkylazido, arylazido, alkyarylazido, arylalkylazido, alkyloxyamino, aryloxyamino, alkyaryloxyamino, arylalkyloxyamino, alkynyl, cycloalkynyl, and alkynylarylalkylcarbonyl, $R^3$ is alkyl, n is an integer of 1 to 10, $R^7$ is hydrogen or alkyl, and $A^1$ and $A^2$ are the same or different and are amino acid moieties, (ii) providing a second component which is $NAD^+$ or an $NAD^+$ analog, wherein the $NAD^+$ analog has the formula:

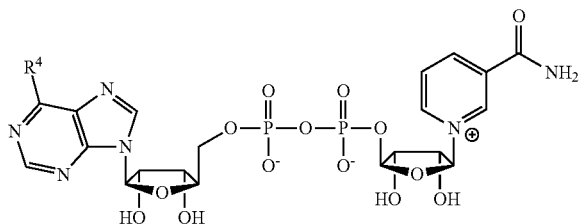

wherein $R^4$ is alkyloxyamino, aminooxyethyleneoxyamino, aminooxyethyleneoxyazido, aminooxy(polyethyleneoxy)amino, or azido(polyethyleneoxy)amino, (iii) providing a third component comprising a sirtuin, and (iv) combining the first, second, and third components such that a sirtuin complex is formed, wherein the sirtuin complex comprises the sirtuin, the sirtuin substrate, and $NAD^+$ or the $NAD^+$ analog, and wherein the sirtuin substrate is a substrate for at least one sirtuin selected from SirT1, SirT2, SirT3, SirT4, SirT5, SirT6, and SirT7.

2. The method of claim 1, wherein the sirtuin substrate is selected from:

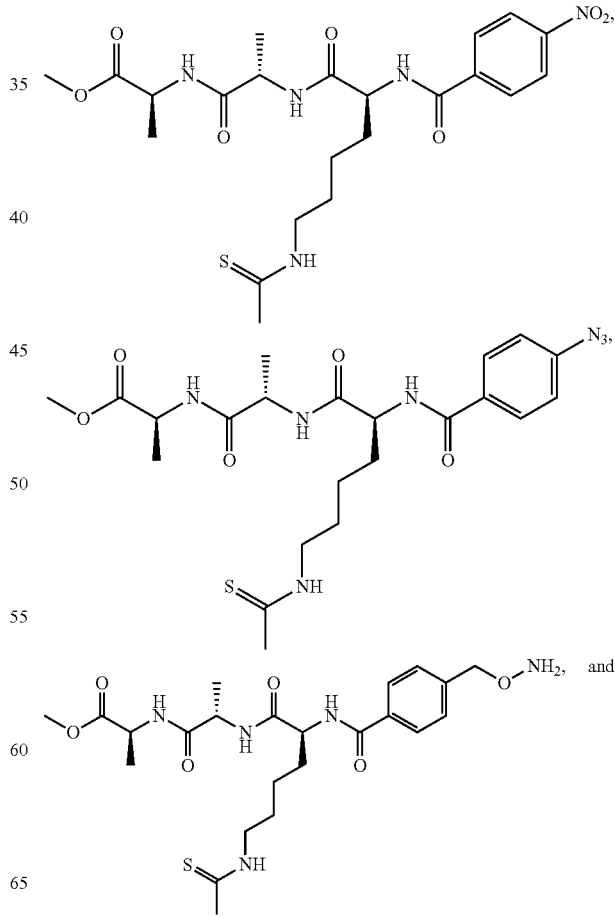

-continued

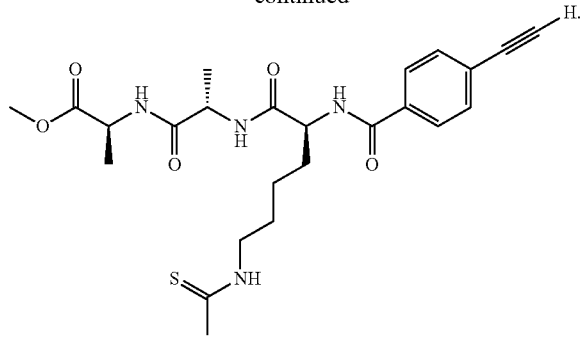

3. A sirtuin complex prepared by the method of claim 1.
4. A method for detecting a sirtuin in a sample, which method comprises:
(i) providing a first component which is a sirtuin substrate having the formula:

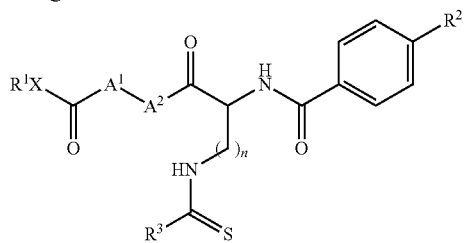

wherein $R^1$ is hydrogen, optionally substituted alkyl or optionally substituted aryl,
X is O or $NR^7$,
$R^2$ is selected from azido, alkylazido, arylazido, alkyarylazido, arylalkylazido, alkynyl and cycloalkynyl,
n is an integer of 1 to 10,
$R^3$ is alkyl,
$R^7$ is hydrogen or alkyl, and
$A^1$ and $A^2$ are the same or different and are amino acid moieties,
(ii) providing a second component which is $NAD^+$ or an $NAD^+$ analog, wherein the $NAD^+$ analog has the formula:

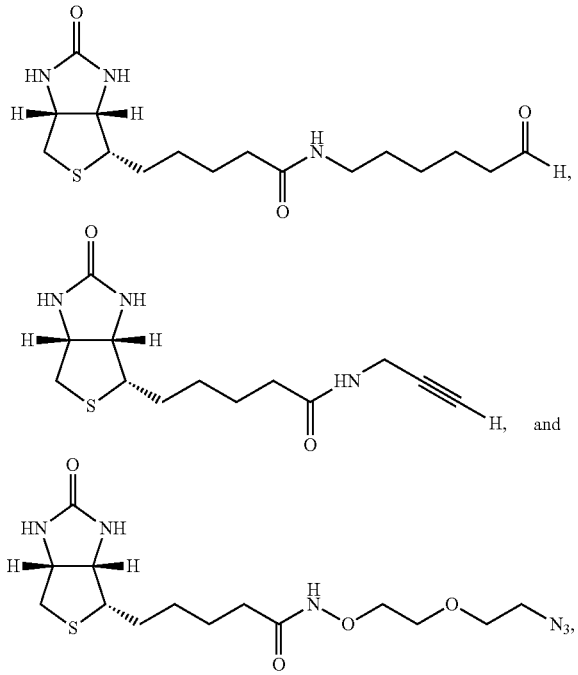

wherein $R^4$ is alkyloxyamino, aminooxyethyleneoxyamino, aminooxyethyleneoxyazido, aminooxy(polyethyleneoxy)amino, or azido(polyethyleneoxy)amino,
(iii) providing a sample suspected of comprising a sirtuin,
(iv) combining the first and second components and sample such that a first mixture is formed, in which the sirtuin, if present in the sample, forms a sirtuin complex,
(v) contacting the first mixture containing the sirtuin complex with a label compound to form a second mixture comprising a labeled sirtuin complex, wherein the label compound is covalently bonded to the sirtuin complex, wherein the label compound is selected from 5-carboxytetramethylrhodamine-azide,

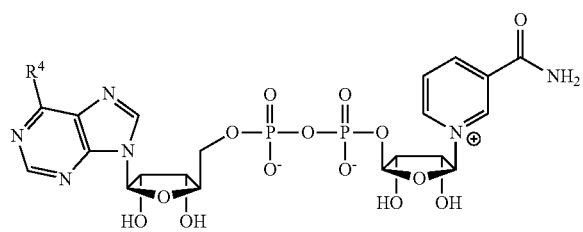

, and (vi) separating the labeled sirtuin complex from other components of the second mixture to form a third mixture, and
(vii) detecting whether the labeled sirtuin complex is present in the third mixture, wherein the detection of the labeled sirtuin complex in the third mixture indicates the presence of the sirtuin in the sample.
5. The method of claim 4, further comprising wherein the separating step (vi) comprises the following steps:
(vi-1) contacting the second mixture with a solid phase so as to immobilize the labeled sirtuin complex, and
(vi-2) separating uncomplexed components from the solid phase to form a third mixture comprising the solid phase and the immobilized sirtuin complex,
(vi-3) optionally, subjecting the solid phase to conditions to regenerate the sirtuin from the labeled sirtuin complex to form a fourth mixture, and
(vi-4) optionally, detecting whether the sirtuin is in the fourth mixture, wherein the detection of the sirtuin in the fourth mixture indicates the presence of the labeled sirtuin complex in the third mixture and thus the presence of the sirtuin in the sample.
6. A method of screening for compounds which inhibit the deacetylase activity of at least one sirtuin, which method comprises:
(i) providing a first test mixture comprising (a) a sirtuin substrate, (b) $NAD^+$, and (c) a candidate compound, wherein the sirtuin substrate has the formula:

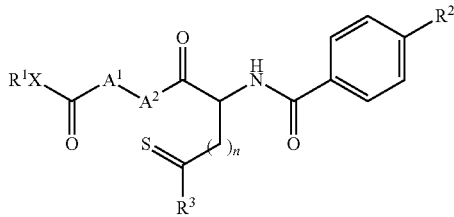

wherein R¹ is hydrogen, optionally substituted alkyl or optionally substituted aryl,
X is O or NR⁷,
R² is selected from azido, alkylazido, arylazido, alkyarylazido, arylalkylazido, alkynyl, cycloalkynyl, and alkynylarylalkylcarbonyl,
n is an integer of 1 to 10,
R³ is alkyl,
R⁷ is hydrogen or alkyl, and
A¹ and A² are the same or different and are amino acid moieties,
(ii) adding a sirtuin to the first test mixture to form a second test mixture,
(iii) incubating the second test mixture for a period of time,
(iv) adding a label compound comprising a second reactive moiety to the second test mixture to form a third test mixture, wherein the first and second reactive moieties react to form at least one covalent bond between the sirtuin substrate and the label compound, wherein the label compound is selected from 5-carboxytetramethyl-rhodamine-azide,

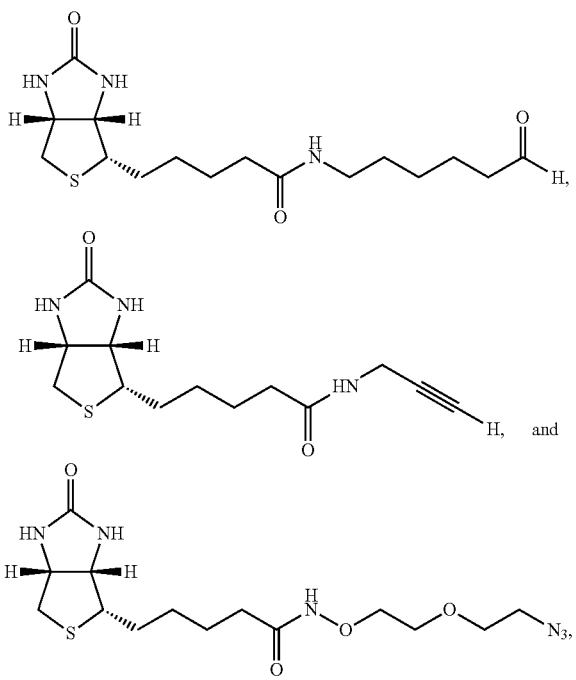

(v) contacting the third test mixture with a solid phase so as to immobilize components comprising the label compound and to form a test solid phase,
(vi) separating uncomplexed components from the test solid phase,
(vii) subjecting the test solid phase to conditions to regenerate the sirtuin, if present, from the test solid phase and to form a fourth test mixture, and
(viii) determining if the sirtuin is present in a decreased amount in the fourth test mixture relative to the amount of sirtuin added to the first test mixture,
wherein a decreased amount of the sirtuin in the fourth test mixture relative to the amount of sirtuin that would be observed in the absence of the candidate compound indicates that the candidate compound is an inhibitor of the sirtuin.

7. The method of claim 6, wherein R¹ and R³ are both alkyl, wherein A¹ and A² are both L-alaninyl moieties, and wherein n is 4.

8. The method of claim 6, further comprising the steps of:
(i') providing a first control mixture comprising (a) the sirtuin substrate comprising a thioamide moiety and a first reactive moiety and (b) NAD⁺,
(ii') adding the sirtuin to the first control mixture to form a second control mixture,
(iii') incubating the second control mixture for a period of time,
(iv') adding the label compound to form a third control mixture, wherein the first and second reactive moieties react to form at least one covalent bond between the sirtuin substrate and the label compound,
wherein the label compound is

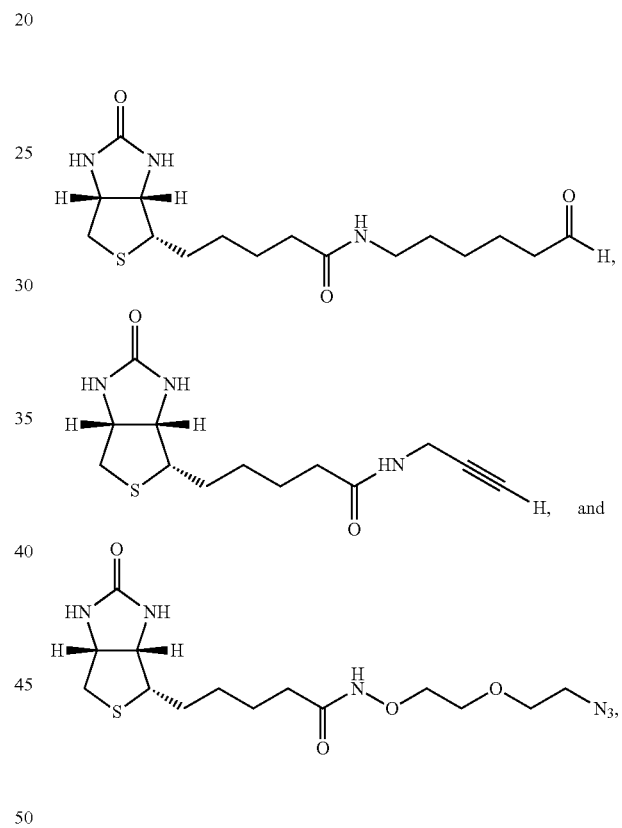

(v') contacting the third control mixture with a solid phase so as to immobilize components comprising a biotin moiety and to form a control solid phase,
(vi') separating uncomplexed components from the control solid phase,
(vii') subjecting the control solid phase to conditions to regenerate the sirtuin from the control solid phase and to form a fourth control mixture, and
(viii') determining if the sirtuin is present in a decreased amount in the fourth test mixture relative to the fourth control mixture,
wherein a decreased amount of the sirtuin in the fourth test mixture indicates that the candidate compound is an inhibitor of the sirtuin.

9. A compound of the formula:

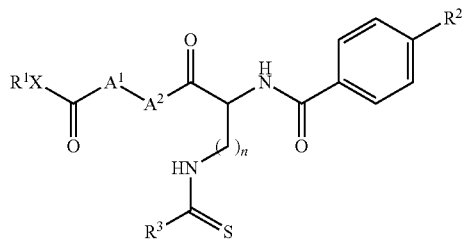

wherein R¹ is hydrogen, optionally substituted alkyl or optionally substituted aryl, X is O or NR⁷, R² is selected from azido, nitro, alkylazido, arylazido, alkyarylazido, arylalkylazido, alkyloxyamino, aryloxyamino, alkyaryloxyamino, arylalkyloxyamino, alkynyl, cycloalkynyl, and alkynylarylalkylcarbonyl, A¹ and A² are the same or different and are amino acid moieties, R³ is alkyl, R⁷ is hydrogen or alkyl, and n is an integer of 1 to 10.

10. The compound of claim 9, wherein the compound is selected from:

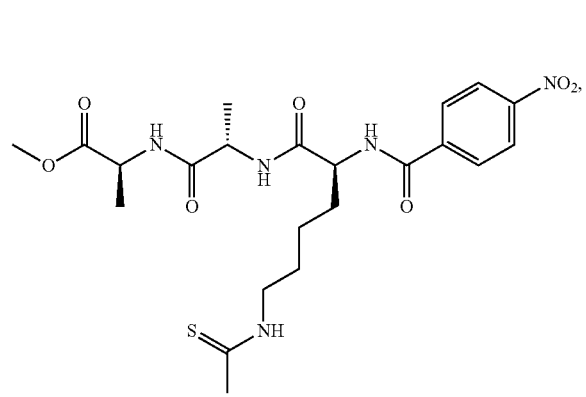

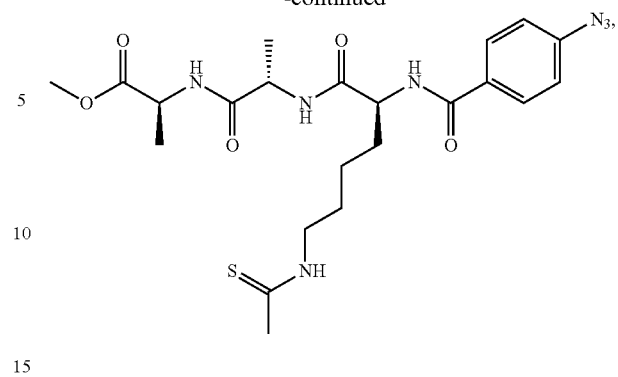

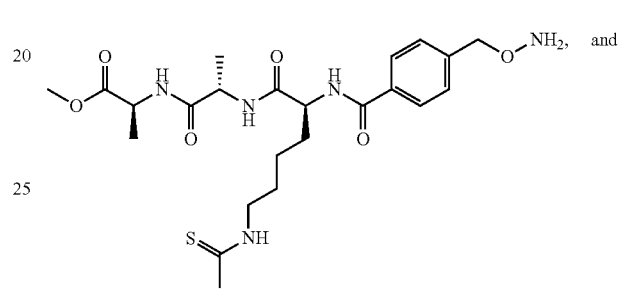

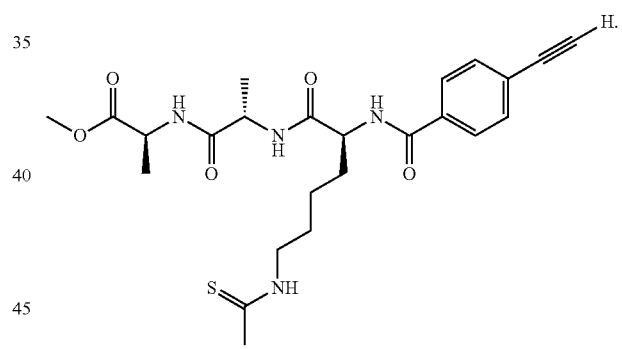

11. A compound of the formula:

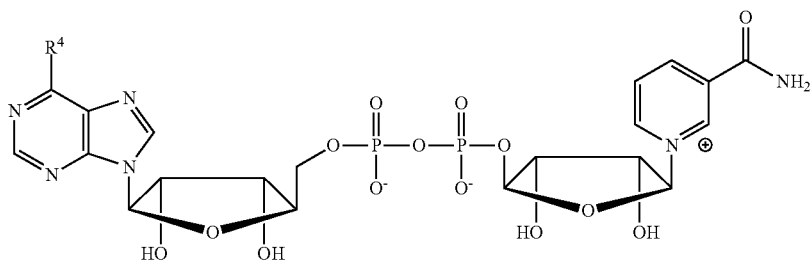

wherein R⁴ is alkyloxyamino, aminooxyethyleneoxyamino, aminooxyethyleneoxyazido, alkylazido, aminooxy(polyethyleneoxy)amino, or azido(polyethyleneoxy)amino.

12. The compound of claim 11, wherein the compound is:

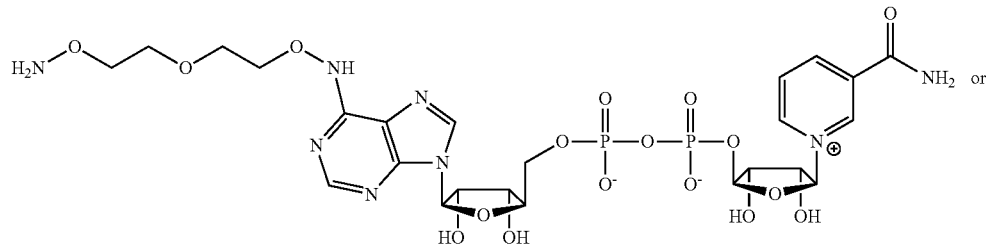

or

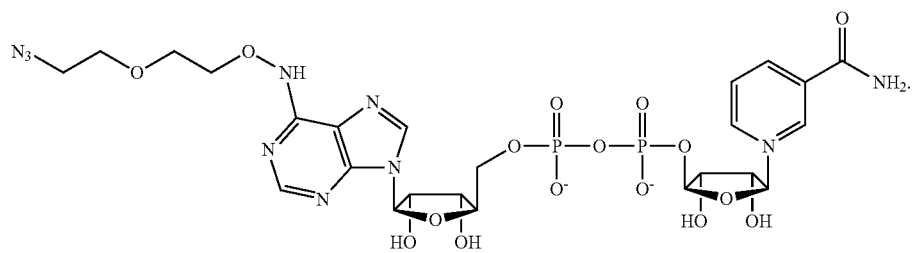

13. A method of preparing a sirtuin complex, which method comprises:
(i) providing a first component comprising a sirtuin substrate comprising a thioamide moiety, wherein the sirtuin substrate has the formula:

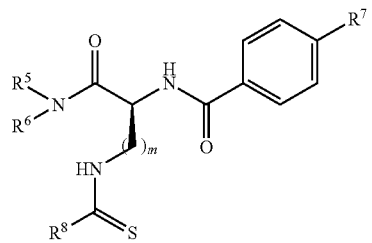

wherein m is an integer of 1 to 10, and wherein $R^5$ and $R^6$ are independently selected from alkyl, aryl, alkoxyalkyl, alkenyl, arylalkyl, and heterocyclyl, or, taken together, form a 3- to 6-membered nitrogen-containing ring, wherein $R^8$ is alkyl, and wherein $R^7$ is selected from hydrogen, alkyl, halo, azido, nitro, alkylazido, arylazido, alkyarylazido, arylalkylazido, alkyloxyamino, aryloxyamino, alkyaryloxyamino, arylalkyloxyamino, alkynyl, cycloalkynyl, and alkynylarylalkylcarbonyl, (ii) providing a second component comprising $NAD^+$ or an $NAD^+$ analog, wherein the $NAD^+$ analog has the formula:

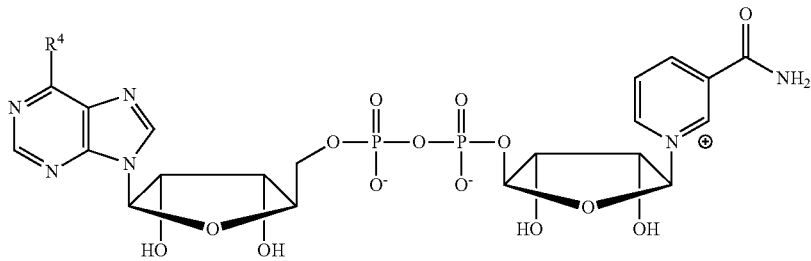

wherein R⁴ is alkyloxyamino, aminooxyethyleneoxyamino, aminooxyethyleneoxyazido, alkylazido, aminooxy(polyethyleneoxy)amino, or azido(polyethyleneoxy)amino, (iii) providing a third component comprising a sirtuin, and (iv) combining the first, second, and third components such that a sirtuin complex is formed, wherein the sirtuin complex comprises the sirtuin, the sirtuin substrate, and NAD⁺ or an NAD⁺ analog, and wherein the sirtuin substrate is a substrate for at least one sirtuin selected from SirT1, SirT2, SirT3, SirT4, SirT5, SirT6, and SirT7.

* * * * *